US012285556B2

United States Patent
Walls et al.

(10) Patent No.: US 12,285,556 B2
(45) Date of Patent: Apr. 29, 2025

(54) AUTOMATED FLUID INFUSION CONTROL FOR CIRCULATORY SUPPORT AND ECMO SYSTEMS

(71) Applicant: Zoll Circulation, Inc., San Jose, CA (US)

(72) Inventors: George L. Walls, San Jose, CA (US); Richard A. Helkowski, Redwood City, CA (US); John Thomas Buckley, San Jose, CA (US)

(73) Assignee: Zoll Circulation, Inc., San Jose, CA (US)

( * ) Notice: Subject to any disclaimer, the term of this patent is extended or adjusted under 35 U.S.C. 154(b) by 490 days.

(21) Appl. No.: 17/133,218

(22) Filed: Dec. 23, 2020

(65) Prior Publication Data

US 2021/0196881 A1 Jul. 1, 2021

Related U.S. Application Data

(60) Provisional application No. 62/954,320, filed on Dec. 27, 2019.

(51) Int. Cl.
*A61M 1/36* (2006.01)
*A61M 1/16* (2006.01)
*A61M 39/28* (2006.01)

(52) U.S. Cl.
CPC .......... *A61M 1/367* (2013.01); *A61M 1/3607* (2014.02); *A61M 1/3609* (2014.02); *A61M 1/3626* (2013.01); *A61M 39/28* (2013.01); *A61M 1/1698* (2013.01); *A61M 2202/0007* (2013.01); *A61M 2205/3334* (2013.01); *A61M 2205/3553* (2013.01); *A61M 2205/50* (2013.01)

(58) Field of Classification Search
CPC .. A61M 1/367; A61M 1/3607; A61M 1/3609; A61M 1/342; A61M 5/1723; A61M 2205/52; A61M 2205/3334; A61M 2205/3553; A61M 2205/05; A61M 2230/005
See application file for complete search history.

(56) References Cited

U.S. PATENT DOCUMENTS 5,356,593 A * 10/1994 Heiberger ........... A61M 1/3609 422/82.11
5,810,759 A * 9/1998 Merz ................... A61M 1/1698 604/6.14

(Continued)

*Primary Examiner* — Rebecca E Eisenberg
*Assistant Examiner* — Matthew Wrubleski
(74) *Attorney, Agent, or Firm* — Fish & Richardson P.C.

(57) ABSTRACT

The present disclosure provides systems for controlling infusion of one or more supplements into blood received from a patient. The systems include at least one an extracorporeal circulatory support system including a pump, fluid conduits, and at least one a sensor configured to measure one or more parameters of the blood. The system also may include a fluid flow regulator coupled to the extracorporeal circulatory support system. The system receives measurement signals corresponding to parameters of blood from the at least one sensor and determines one or more target values for the parameters of blood based on a patient profile and/or the measurements. The system may control the fluid flow regulator to cause an infusion of at least one supplemental fluid from a supplemental fluid source into the blood.

20 Claims, 19 Drawing Sheets

(56) References Cited

U.S. PATENT DOCUMENTS

| | | | | |
|---|---|---|---|---|
| 6,090,061 | A * | 7/2000 | Steuer | A61M 1/3609 |
| | | | | 604/4.01 |
| 2011/0208107 | A1* | 8/2011 | Muller-Spanka | A61M 1/3626 |
| | | | | 604/6.11 |
| 2013/0020237 | A1* | 1/2013 | Wilt | A61M 1/301 |
| | | | | 210/85 |
| 2013/0267884 | A1* | 10/2013 | Boggs | A61M 1/36225 |
| | | | | 604/6.02 |
| 2014/0039446 | A1* | 2/2014 | Day | G16H 40/40 |
| | | | | 604/67 |
| 2014/0069868 | A1* | 3/2014 | Nguyen | A61M 1/303 |
| | | | | 210/196 |
| 2016/0220748 | A1* | 8/2016 | Pouchoulin | A61M 1/1601 |
| 2020/0061281 | A1* | 2/2020 | Desouza | A61M 1/3663 |
| 2020/0230309 | A1* | 7/2020 | Treu | A61M 1/1656 |

\* cited by examiner

AUTOMATED FLUID INFUSION CONTROL FOR CIRCULATORY SUPPORT AND ECMO SYSTEMS

CLAIM OF PRIORITY

This application claims priority under 35 U.S.C. § 119(e) to U.S. Patent Application Ser. No. 62/954,320, filed on Dec. 27, 2019, the entire contents of which are hereby incorporated by reference.

TECHNICAL FIELD

The present application relates generally to the field of extracorporeal circulatory support system systems.

BACKGROUND

Extracorporeal circulatory support systems are used to provide critical life supporting assistance to patient blood fluids outside of the body of the patient. Extracorporeal circulatory support systems can include systems such as extracorporeal membrane oxygenation systems, which can provide oxygenation and carbon dioxide removal, to blood if the lungs or heart of a patient is incapacitated, non-functional, or inadequate, for example, during or after cardiac or respiratory surgery, during respiratory, cardiac, or cardiorespiratory failure, etc. Such systems can provide life-preserving functions for a patient outside of the body of the patient while the underlying condition or failure is treated or repaired. These systems can provide partial support or full support for heart and lung functions as a patient is treated.

SUMMARY

Example systems for controlling infusion of one or more supplements into blood received from a patient are disclosed. The systems include at least one extracorporeal circulatory support system. The systems also include a pump. The systems also include a plurality of fluid conduits fluidly coupled to the pump through which the blood flows. The systems also include at least one sensor configured to measure one or more parameters of the blood. The systems also include at least one fluid flow regulator coupled to the extracorporeal circulatory support system. The systems also include a processor, a memory, and associated circuitry communicatively coupled to the at least one sensor and the at least one fluid flow regulator, where the processor is configured to receive one or more signals corresponding to measurements of the one or more parameters of blood from the at least one sensor, determine one or more target values for the one or more parameters of blood received from the patient, based on a patient profile and the one or more signals and control the at least one fluid flow regulator to cause an infusion of at least one supplemental fluid from a supplemental fluid source into the blood to modify at least one of a content and a state of the blood, based on the one or more determined target values.

In some implementations, the processor is configured to receive data corresponding to a parameter of the at least one supplemental fluid infused into the blood.

In certain implementations, the processor is configured to cause the at least one sensor to measure the one or more parameters of the blood after the infusion of the at least one supplemental fluid, and to continue infusion if the post infusion measured parameter of the blood does not correspond to the one or more target values or stop infusion if the post infusion measured parameter of the blood corresponds to the target value.

In particular implementations, the processor is configured to cause the patient profile to be updated during a treatment cycle based on the one or more measured parameters of the blood after the infusion of the at least one supplemental fluid.

In some implementations, the patient profile includes a present log comprising patient data detected and stored in the present log.

In certain implementations, the processor is configured to access the patient profile via the memory to determine the one or more target values for the one or more parameters of blood received from the patient.

In particular implementations, the processor is configured to access the patient profile via a remote server to determine the one or more target values for the one or more parameters of blood received from the patient.

In some implementations, the at least one extracorporeal circulatory support system includes an extracorporeal membrane oxygenation machine.

In certain implementations, the extracorporeal circulatory support system includes an automated clamp or valve and wherein the processor system is configured to cause one or more supplements from the at least one supplemental fluid source to be infused during an unclamped phase or open valve phase.

In particular implementations, the open valve phase includes a fully open valve phase and a partially open valve phase.

In some implementations, the extracorporeal membrane oxygenation machine includes an oxygenator.

In certain implementations, the extracorporeal membrane oxygenation machine includes an arterial filter positioned downstream of the oxygenator.

In particular implementations, the extracorporeal membrane oxygenation machine includes a bubble sensor.

In some implementations, the extracorporeal membrane oxygenation machine includes a pressure sensor.

In certain implementations, the fluid flow regulator includes an infusion pump.

In particular implementations, the at least one supplemental fluid source includes a plurality of supplemental fluid sources and wherein the processor is configured to select a supplemental fluid source from the plurality of supplemental fluid sources based on the one or more target values of the one or more parameters for the blood.

In some implementations, the plurality of supplemental fluid sources include blood, saline, and medication.

In certain implementations, the at least one sensor includes an infusion sensor configured to measure one or more of a duration, a flow rate, and a pressure of the at least one supplemental fluid source infused into the blood.

In particular implementations, the systems include an alarm system communicably coupled to the processor and configured to provide a notification when the at least one supplemental fluid source is infused into the blood.

In some implementations, processor is configured to infuse the at least one supplemental fluid source into the blood until the one or more measured parameters for the blood reach the one or more target values.

In certain implementations, the processor is configured to cause storage of data corresponding to the quantity of the at least one supplemental fluid source infused into the blood.

In particular implementations, the systems include a flow detector configured to determine a volume of the supplemental fluid infused into the blood via the at least one fluid flow regulator.

In some implementations, the processor is configured to cause storage of the volume of supplemental fluid infused into the blood in an infusion log for each infusion cycle.

In certain implementations, the processor system is configured to cause a dynamic display to display the infusion log of the volume of supplemental fluid infused into the blood.

In particular implementations, the sensor includes a temperature sensor configured to sense a temperature of one or more of the blood and of the supplemental fluid infused into the blood.

In some implementations, the sensor includes a pH sensor configured to sense a pH of one or more of the blood and of the supplemental fluid infused into the blood.

In certain implementations, the sensor includes a pressure sensor configured to sense a pressure of one or more of the blood and of the supplemental fluid infused into the blood.

In particular implementations, the sensor includes an oxygen sensor and a flow sensor.

In some implementations, the sensor includes an oxygen sensor and a pressure sensor.

In certain implementations, the sensor includes a hemoglobin sensor.

In particular implementations, the sensor includes a hematocrit sensor.

In some implementations, the sensor includes a carbon dioxide sensor.

Example methods for controlling infusion of one or more supplements into blood received from a patient are disclosed. The methods include measuring, via one or more sensors, one or more parameters of the blood received from the patient in an extracorporeal circulatory support system. The methods include transmitting one or more signals to a processor, the one or more signals corresponding to the one or more measured parameters. The methods include determining, by the processor, one or more target values for the one or more parameters of blood received from the patient, based on a patient profile and the one or more signals. The methods include causing an infusion of at least one supplemental fluid from a supplemental fluid source into the blood to modify at least one of a content and a state of the blood, based on the one or more determined target values. The methods include receiving data corresponding to a parameter of the at least one supplemental fluid infused into the blood. The methods include measuring, via the one or more sensors, the one or more parameters of the blood after the infusion of the at least one supplemental fluid. The methods include continuing to cause infusion if the measured one or more parameters of the blood after infusion do not correspond to the target value or stopping infusion if the measured one or more parameters of the blood after infusion correspond to the target value.

In certain implementations, the methods include updating the patient profile during a treatment cycle based on the one or more measured parameters of the blood after the infusion of the at least one supplemental fluid.

In particular implementations, determining one or more target values for the one or more parameters of blood received from the patient includes determining based on a patient profile including a present log comprising patient data measured and stored in the present log.

In some implementations, the extracorporeal circulatory support system includes an extracorporeal membrane oxygenation machine and the measured one or more parameters includes oxygen saturation.

In certain implementations, causing an infusion includes at least one of partially or completely opening a valve and partially or completely releasing a clamp.

In particular implementations, causing an infusion includes activating an infusion pump.

In some implementations, causing an infusion includes selecting a supplemental fluid source from a plurality of supplemental fluid sources based on the one or more target values of the one or more parameters for the blood.

In certain implementations, the plurality of supplemental fluid sources comprise blood, saline, and medication.

In particular implementations, the one or more parameters of the blood includes one or more of quantity, flow rate, pressure, type, and temperature.

In some implementations, the methods include sensing a duration of the infusion of the at least one supplemental fluid.

In some implementations, the methods include sensing a flow rate of the infusion of the at least one supplemental fluid.

In particular implementations, the methods include determining a volume of the supplemental fluid infused into the blood via the at least one fluid flow regulator.

In certain implementations, the methods include sensing a pressure of the at least one supplemental fluid.

In some implementations, the methods include generating an alarm configured to provide a notification when the at least one supplemental fluid source is infused into the blood.

In particular implementations, the methods include storing data corresponding to a quantity of the at least one supplemental fluid source infused into the blood.

In certain implementations, the methods include transmitting the quantity of the at least one supplemental fluid source infused into the blood to a remote server system.

In some implementations, the methods include causing a dynamic display to display a log of volumes of supplemental fluid infused into the blood.

In particular implementations, the methods include transmitting the log of volumes of supplemental fluid infused in the blood to a remote server system.

In certain implementations, causing an infusion of at least one supplemental fluid into the blood, responsive to the one or more determined target values includes infusing the at least one supplemental fluid source into the blood until the one or more measured parameters for the blood reach the one or more target values.

In some implementations, the methods include sensing a temperature of one or more of the blood and of the supplemental fluid infused into the blood.

In particular implementations, the methods include sensing a pressure of one or more of the blood and of the supplemental fluid infused into the blood.

In certain implementations, the methods include sensing a pH of one or more of the blood and of the supplemental fluid infused into the blood.

Example systems for controlling blood for supporting a patient are disclosed. The systems include at least one extracorporeal circulatory support system. The systems include a pump. The systems include a plurality of fluid conduits fluidly coupled to the pump through which the blood flows. The systems include an oxygenator fluidly coupled to at least one fluid conduit of the plurality of fluid conduits. The systems include a reservoir fluidly coupled to the plurality of fluid conduits. The systems include at least one sensor configured to measure one or more of fluid pressure, fluid volume, and fluid constituents in the at least one extracorporeal circulatory support system. The systems include at least one fluid flow regulator coupled to the extracorporeal circulatory support system. The systems include a processor, a memory, and associated circuitry communicatively coupled to the at least one sensor and the at least one fluid flow regulator, wherein the processor system is configured to: receive one or more signals corresponding to measurements of the one or more parameters of blood from the at least one sensor, determine one or more target values for the one or more parameters of blood received from the patient based on a patient profile and the one or more signals, and control the at least one fluid flow regulator to cause an infusion of at least one supplemental fluid from a supplemental fluid source into the blood to modify at least one of a content and a state of the blood, based on the one or more determined target values.

Example systems for controlling blood parameters in an extracorporeal blood circuit are disclosed. The systems include at least one extracorporeal circulatory support system. The systems include a pump. The systems include a plurality of fluid conduits fluidly coupled to the pump through which the blood flows. The systems include at least one sensor configured to measure one or more parameters of the blood. The systems may include at least one fluid flow regulator coupled to the extracorporeal circulatory support system. The systems include a processor, a memory, and associated circuitry communicatively coupled to the at least one sensor and the at least one fluid flow regulator, wherein the processor is configured to: receive one or more signals corresponding to measurements of the one or more parameters of blood from the at least one sensor, determine one or more target values for the one or more parameters of blood received from the patient, based on a patient profile and the one or more signals, and control the speed of the blood pump based on the one or more determined target values.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

The features and advantages of the inventive subject matter disclosed herein will become more apparent from the detailed description set forth below when taken in conjunction with the drawings.

DETAILED DESCRIPTION

The following disclosure describes systems and methods related to, and exemplary embodiments of, inventive infusion control and/or blood parameter control systems, methods and components. The systems may permit supplemental fluids, such as saline, medication, and blood contents to be delivered to a patient blood circuit in a controlled and highly targeted fashion. The infusion of such fluids can be accurately and automatically measured and reported so that service providers can easily retain records of how much fluid has been administered to a patient and accurately and safely provide such services via the system.

Figure 1:
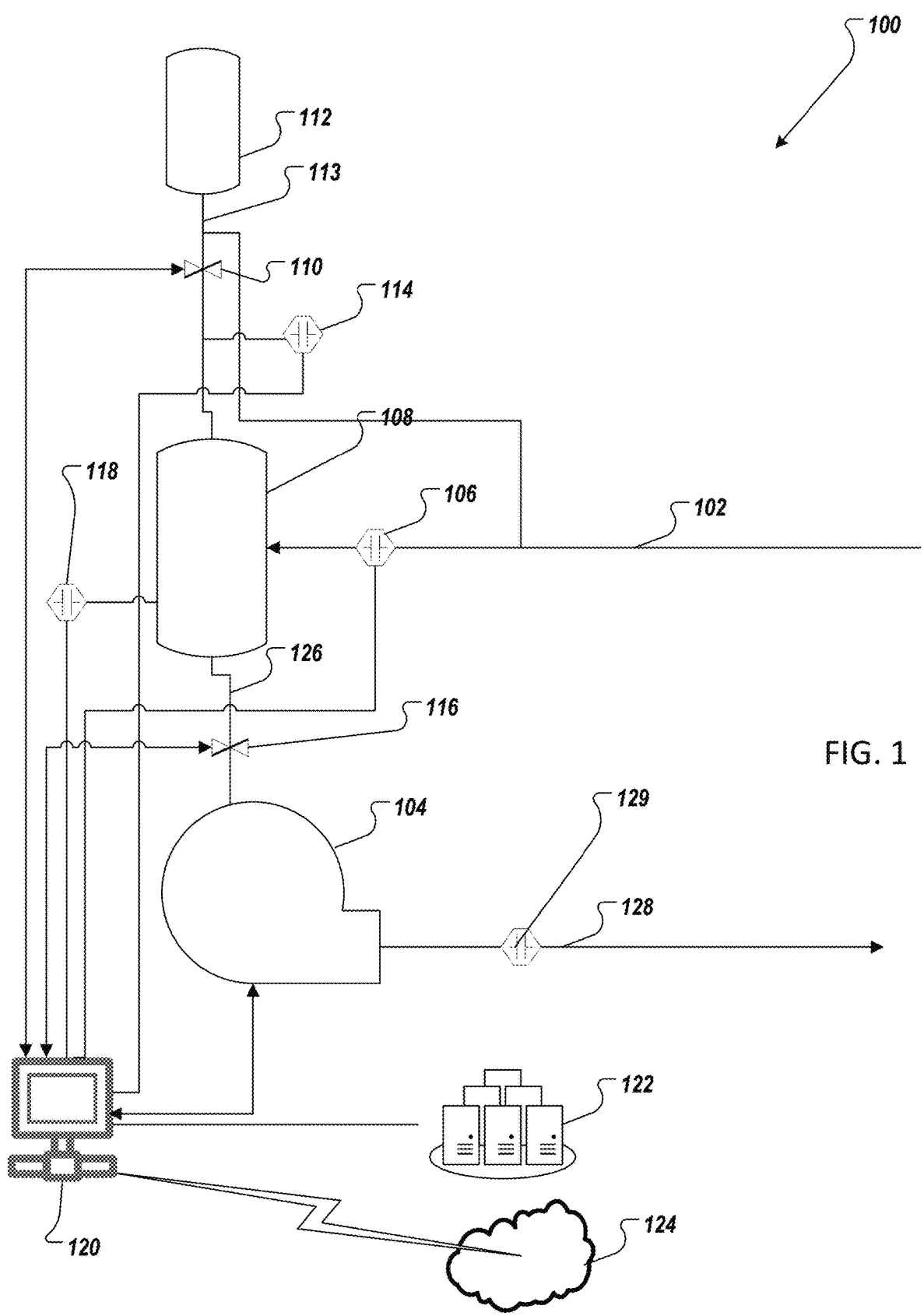
FIG. 1 is a schematic diagram of a system for controlling infusion of one or more supplements into blood received from a patient.

FIG. 1 illustrates a system 100 capable of controlling infusion of one or more supplements into blood received from a patient and/or capable of controlling blood parameters in an extracorporeal blood circuit, e.g., by regulating blood pump speed according to one implementation of the present disclosure. The system 100 receives blood from a patient via a venous line 102. One or more sensors 106 is fluidly coupled to the venous line 102 to detect a property of the blood being received from the patient. The sensor(s) 106 can measure various blood parameters, e.g., oxygen level, flow rate, pressure, hemoglobin content, hematocrit content, pH, CO2 level, and/or temperature. The sensor(s) 106 is communicably coupled to a control system 120. The control system 120 includes a processor, a memory, and associated circuitry for controlling flow of the blood and/or infusion of one or more supplemental fluids, e.g., Oxygen, CO2, bicarbonate, or red blood cells, into the blood received from the patient pursuant to a processor-readable computer program providing a set of instructions stored on a memory device (either local or remote) and based on a stored patient profile (either local or remote) and the measured blood parameters of the blood. In certain implementations, the blood received from the patient may be pumped to a blood reservoir 108, for example, via pump 104 fluidly coupled to the reservoir via one or more valves 116 or via a separate pump providing a pressure differential over venous line 102. In certain implementations, the sensor(s) 106 may be positioned in the blood reservoir 108 or elsewhere in the system, e.g., on or in the venous or arterial lines. In certain implementations, certain ones of the sensors 106 may be positioned along the venous line 102, while other sensors may be positioned in the reservoir 108 and or the arterial line 128. In certain implementations, the system may not include a reservoir and one or more of the sensors 106 may be positioned along the venous line and/or the arterial line, or elsewhere in the system. The system 100 may include or be configured to be fluidly coupled to one or more supplemental reservoirs, containers or other supplemental fluid source 112 for infusion of one or more supplements into the blood received from the patient and/or contained in the reservoir 108. The supplements 112 can include supplemental fluids such as blood, saline, gas, and/or medication. The implementations including multiple supplemental fluids may include multiple containers containing each of the fluids, or a single container with multiple chambers for keeping different supplemental fluids separate, which may be independently added or infused into the patient blood retained in the pump, fluid conduits, reservoir 108, or other components through which blood flows in the extracorporeal blood circuit. The supplemental fluid container 112 may be fluidly coupled to the blood venous line 102 or reservoir 108 via a fluid conduit 113. A valve 110, communicably coupled to the control systems 120 can be controlled (fully or partially opened or closed) to permit transmission of a supplemental fluid from supplemental reservoir 112 into the venous line or blood reservoir 108. One or more sensors 114 can be positioned along the fluid conduit 113 for sensing properties such as pressure, flow rate, duration run, quantity, or other parameters of the supplemental fluid obtained from the supplemental container 112. In some implementations, an active component such as an infusion pump or a fluid source clamp may be used in place of or in concert with the valve 110 for actively pumping the supplemental fluid from the supplemental container 112. The infusion pump can also be communicably coupled to the control system 120.

In certain implementations, an exemplary control system 120 may include a controller for processing input information and issuing commands to the various components or elements of the systems described herein. In certain implementations, the controller may incorporate a safety interlock logic block for monitoring and ensuring the system operates within safety parameters. The safety interlock may be implemented with a logic block such as field programmable gate arrays (FPGA). In one implementation, the safety interlock is a decision-tree logic performed by a logic device implemented with a Field Programmable Gate Array (FPGA) chip, which is integrated on the controller printed circuit board (PCB). The FPGA circuitry may be live at start-up. The safety interlock may continuously monitor inputs for events that require treatment stoppage or enable treatment. The safety interlock has the ability to disable all powered electronics in the system. When certain conditions occur, the safety interlock may stop treatment by disabling one or more powered electronics, which automatically closes or stops one or more of the components or elements, e.g., clamps, pumps, fluid flow regulators, and valves.

As discussed in further detail in connection with FIG. 2 and other illustrations provided herein, the control system 120 controls the flow of the supplemental fluid from the supplemental container 112 based, at least in part, on the content and/or state of the blood in the extracorporeal blood circuit, e.g., in the blood reservoir 108. The control system 120 can be communicably coupled to one or more local server systems 122, which can be configured for data storage locally and/or communicably coupled to one or more remote server systems 124 via a network such as the internet. The control system 120 can also include user interface components such as a display, keyboard, or mouse. These components can be used to adjust various parameters and view various reports that may be generated and/or displayed based on the processes executed by the control system. The report content and/or format may be customized by a user. For example, a display can show data logs created that maintain a record of what supplemental fluids were infused, the quantity of those fluids infused, the time of the infusion, the rate of infusion, the reason for infusion, and the results (e.g. sensed parameters of the blood fluid, post infusion) of those infusions. The storage system of the control system 120 can retain this information in a database that can be cataloged based on the patient treated. The storage system of the control system 120 can receive data from a patient profile. A patient profile may include information about the patient being treated, e.g., patient specific blood parameter data such as SO2, pCO2, pO2, pH, Hemoglobin, Hematocrit, blood pressure and/or flow rate. The patient profile may include data regarding acceptable or normal values for blood parameters, such as SO2, pCO2, pO2, pH, Hemoglobin, Hematocrit, blood pressure and/or flow rate, for representative patients or patient populations. The patient population may be based on age, height, weight, sex, and/or various metrics within predefined ranges. The patient specific and/or patient population data in a patient profile may also include medication and allergies, immunization status, laboratory test results, radiology images, vital signs, medical history, billing information, past and current blood parameter values, various demographics, such as age, and/or metrics such as, height and weight. At least some or all of this data may be relevant to the infusion protocol initiated by the control system 120 over a treatment cycle. In certain implementations, the control system 120 is configured to operate in a feedback control loop to continue infusing the supplemental fluid source into the blood or to continue increasing or decreasing pump speed until a target value, which may be a delta or an absolute value, is reached. In such implementations, after an initial infusion is applied, a new sensor reading may be taken of the infused fluid to determine whether or not any further infusions are required. The pump 104 controls pumping of the infused blood 116, through the venous line and to an arterial line 128 for circulating back to the patient. In certain implementations, the blood may be pumped from the venous line, to the blood reservoir 108, and from the blood reservoir 108, via conduit 126 to an arterial line 128 for circulating back to the patient.

Figure 2:
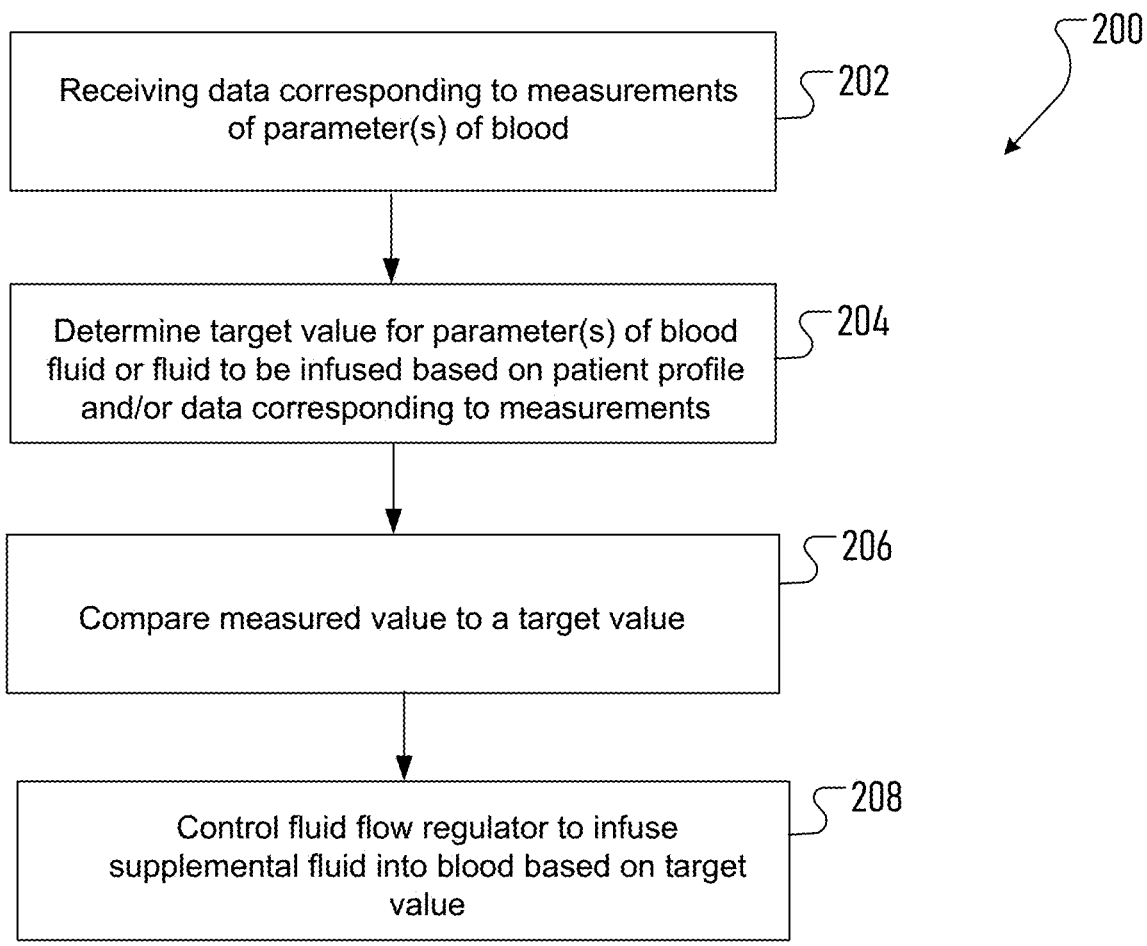
FIG. 2 shows a flow diagram of a system for controlling infusion of one or more supplements into blood received from a patient or controlling a blood pump.

FIG. 2 shows a flow diagram of one implementation of a system for controlling infusion of one or more supplements into blood received from a patient. The system 200 can be implemented via the control system 120 of FIG. 1 using the processor and memory storage device to execute various actions. At 202, the control system 120 receives data corresponding to measurements of one or more parameter(s) of blood fluid received via venous line 102 during treatment. The parameters are obtained from one or more sensors, e.g., sensor(s) 106, 129 for measuring various blood parameters such as SO2, pCO2, pO2, pH, Hemoglobin, Hematocrit, blood pressure and/or flow rate, which sensors may be positioned in one or more locations in or on the extracorporeal blood circuit. At 204, the control system 120 determines a target value for parameter(s) of blood or fluid to be infused. This target value is based, at least in part on data from a patient profile and/or data corresponding to the measurements of one or more parameter(s) of blood received during treatment, such as the parameters detected from the one or more above referenced sensors 106, 129. As discussed supra, the patient profile can include data regarding the specific patient being treated and/or may include data regarding normal or acceptable patient population values as provided in a lookup table, stored on a memory device, or accessible via a wired or wireless network for a patient having metrics within a certain range. The patient profile can include a present log including patient data such as age, weight, sex, and other health criteria or blood properties and/or data regarding prior infusions. The patient profile can include data regarding the specific patient, e.g., past blood parameter data from a previous treatment or blood parameter data measured during the patient's current treatment. At 206, the control system 120 may compare the measured value to the target value or a normal value. At 208, the control system 120 controls a fluid flow regulator (such as, valve 110 or an infusion pump) to infuse or deliver supplemental fluid, e.g., saline or red blood cells, into the blood or controls the blood pump speed, e.g., to adjust blood flow rate, based on the target value or the difference in the measured value and target value. The control system 120 can control the fluid flow regulator to release or deliver the supplemental fluid at a specified flow rate or over a specified period of time depending on the needs of the patient. In some implementations, the control system 120 can generate a notification or alarm whenever supplemental fluids are added to the blood or the blood pump speed changes. In certain implementations, the control system may include a user interface, which may emit a visual or audible alert to indicate the addition of supplemental fluids to the blood and/or the rate of addition and/or quantity of such fluid or the blood pump speed changes.

Figure 3:
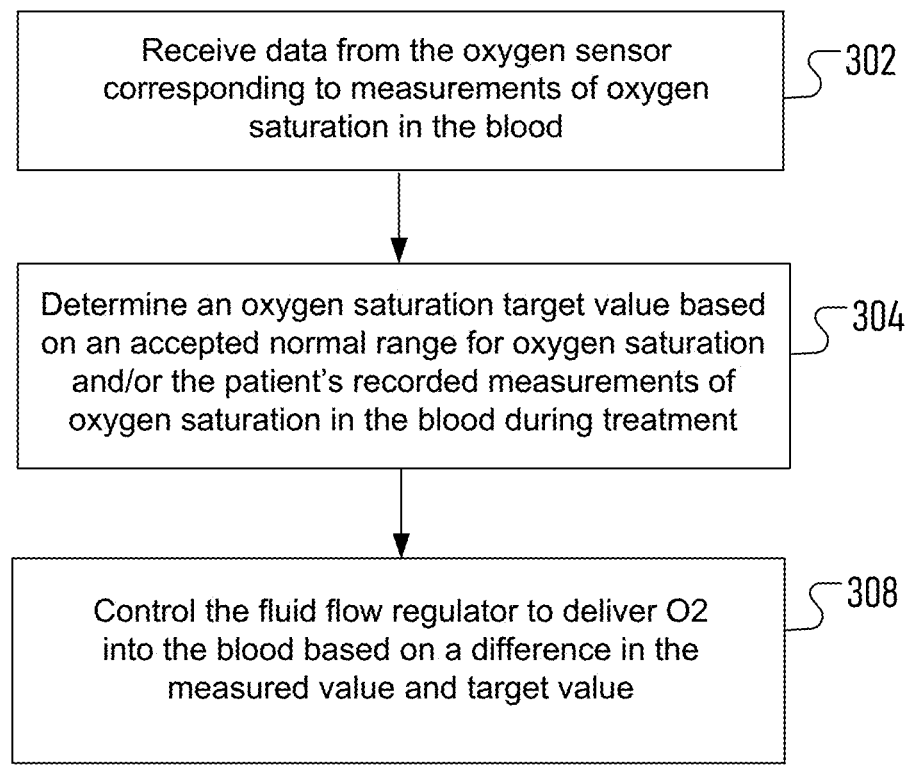
FIG. 3 shows a flow diagram of a system for controlling infusion of one or more supplements into blood received from a patient based on SO2 measurement.

FIG. 3 shows a first example of a flow diagram of a system for controlling infusion or delivery of one or more supplements into blood received from a patient. The system includes an oxygen sensor, e.g., a sensor utilizing optical reflectance technology or a pulse oximeter for measuring oxygen saturation (SO2), e.g., arterial oxygen saturation and/or venous oxygen saturation in the blood. Pulse oximetry estimates the percentage of oxygen bound to hemoglobin in the blood. A pulse oximeter uses light-emitting diodes and a light-sensitive sensor to measure the absorption of red and infrared light. The system can be implemented via the control system 120 of FIG. 1 or FIG. 13 using the processor and memory storage device to execute various actions. The processor is configured to perform the following steps: The processor retrieves a normal range of values for oxygen saturation in a healthy patient having the same height, weight, age and sex as the patient being treated, by accessing a look up table in the patient profile stored locally on the system memory or in a remote database. The accepted normal range for arterial oxygen saturation in a healthy patient is e.g., 90-100 percent. The processor receives a signal from the sensor measuring arterial oxygen saturation in the blood circuit, which indicates a value for the sensed arterial oxygen saturation in the blood during treatment 302. The processor calculates the delta between the average value in the normal range of values for oxygen saturation and the received value for the sensed oxygen saturation of the patient during treatment. The processor determines the target value for the percent oxygen to be delivered to the blood circuit using a standard PID algorithm (see below) and the calculated delta value 304.

$$u(t) = K_p e(t) + K_i \int_0^t e(t')dt' + K_d \frac{de(t)}{dt}$$

Where Kp, Ki, Kd, denote coefficients for the proportional, integral, and derivative terms, t is time, e is the calculated delta (error value), and u is the target value. The processor controls the fluid flow regulator, e.g., an electronic gas blender 733 (which is in fluid communication with the blood carrying conduit and/or an oxygenator of the extracorporeal circulatory support system) to adjust the percentage of oxygen gas delivered to or infused into the blood circuit (via an oxygenator) based on the target value to adjust arterial oxygen saturation 308. The processor continues to receive signals from the sensor measuring arterial oxygen saturation in the blood circuit to monitor the sensed arterial oxygen saturation in the blood during treatment.

When the sensor measuring oxygen saturation in the blood circuit is the sensor that measures venous oxygen saturation in the blood during treatment rather than the arterial oxygen saturation sensor, the processor performs the same steps recited above with the following difference. The normal range for oxygen saturation in the venous blood of a healthy patient is 60-80 percent. The processor controls the speed of the arterial blood pump to adjust the flow rate of blood in the blood circuit based on the target value to adjust venous oxygen saturation. The processor continues to receive signals from the sensor measuring venous oxygen saturation in the blood circuit to monitor the sensed venous oxygen saturation in the blood during treatment.

Figure 4:
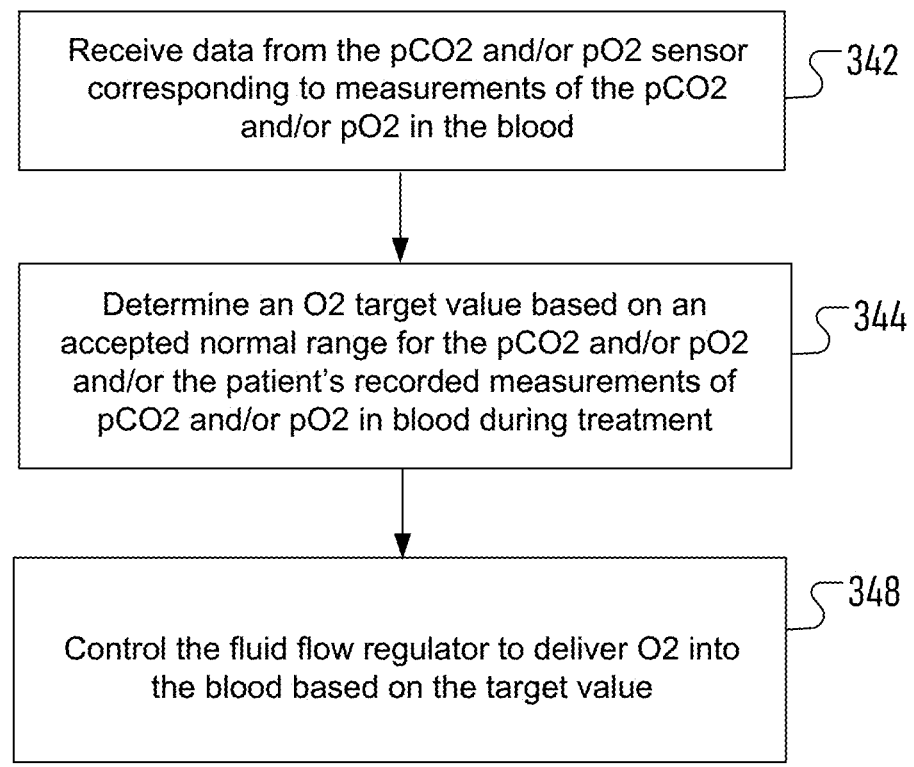
FIG. 4 shows a flow diagram of a system for controlling infusion of one or more supplements into blood received from a patient based on pCO2 and/or pO2 measurement.

FIG. 4 shows a second example of a flow diagram of a system for controlling infusion or delivery of one or more supplements into blood received from a patient. The system includes a pCO2 and/or pO2 sensor, e.g., a fluorescence sensor for measuring the partial pressure of CO2 and/or partial pressure of O2 in the arterial or venous blood. A fluorescence sensor may use optical fluorescence technology to measure CO2 and O2 levels in blood, for example, such as the technology used in the CDI510H shunt sensor provided by Terumo The system can be implemented via the control system 120 of FIG. 1 or FIG. 13 using the processor and memory storage device to execute various actions. The processor is configured to perform the following steps: The processor retrieves a normal range of values for pCO2 or pO2 in a healthy patient having the same height, weight, age and sex as the patient being treated, by accessing a look up table in the patient profile stored locally on the system memory or in a remote database. An accepted normal range in arterial blood may be 35-45 mmHg for the pCO2 and 75-100 mmHg for pO2. The processor receives a signal from the sensor measuring arterial pCO2 or pO2 in the blood circuit, which indicates a value for the sensed arterial pCO2 or pO2 in the blood during treatment 342. The processor calculates the delta between the average value in the normal range of values for pCO2 or pO2 and the received value for the sensed pCO2 or pO2 of the patient during treatment.

For arterial pCO2, the processor determines the target value for the flow rate of oxygen gas being delivered to the blood circuit using a standard PID algorithm (see above) and the calculated delta value 344. For arterial pCO2, the processor controls the fluid flow regulator, e.g., a needle valve 732 which controls the flow of oxygen gas into the blood circuit, to adjust the flow rate of oxygen gas delivered to or infused into the blood circuit (via an oxygenator) based on the target value 348, e.g., to adjust and/or maintain arterial pCO2.

For arterial pO2, the processor determines the target value for the percent oxygen to be delivered to the blood circuit using a standard PID algorithm (see above) and the calculated delta value 344. For arterial pO2, the processor controls the fluid flow regulator, e.g., an electronic gas blender 733 (which is in fluid communication with the blood carrying conduit and/or an oxygenator of the extracorporeal circulatory support system) to adjust the percentage of oxygen gas delivered to or infused into the blood circuit (via an oxygenator) based on the target value 348, e.g., to adjust and/or maintain arterial pO2. The processor continues to receive signals from the sensors measuring arterial pCO2 or pO2 in the blood circuit to monitor the sensed arterial pCO2 or pO2 in the blood during treatment.

Figure 5:
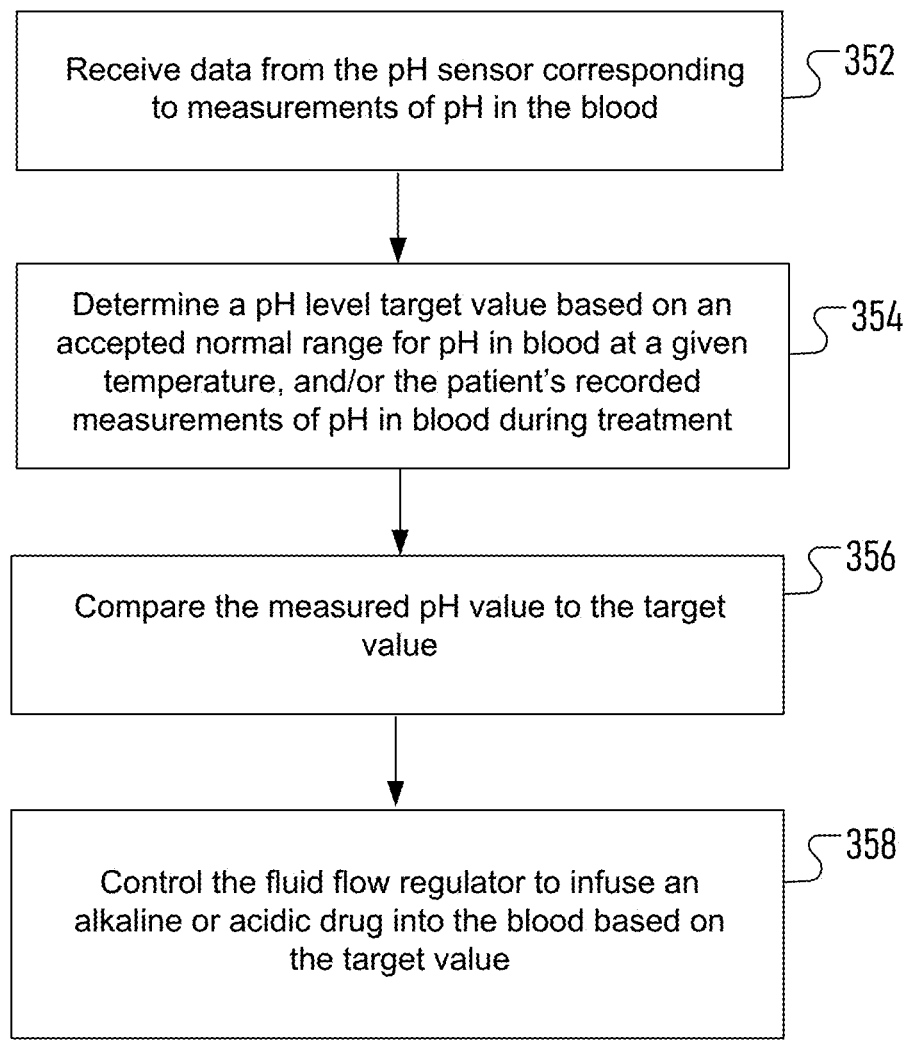
FIG. 5 shows a flow diagram of a system for controlling infusion of one or more supplements into blood received from a patient based on pH measurement.

FIG. 5 shows a third example of a flow diagram of a system for controlling infusion or delivery of one or more supplements into blood received from a patient. The system includes a sensor for measuring pH of the blood, e.g., a fluorescence sensor for measuring pH of the patient's arterial or venous blood. A fluorescence sensor may use optical fluorescence technology to measure a pH of the blood, for example, such as the technology used in the CDI510H shunt sensor provided by Terumo. The system can be implemented via the control system 120 of FIG. 1 or FIG. 13 using the processor and memory storage device to execute various actions. The processor is configured to perform the following steps: The processor retrieves a normal range of values for arterial pH in a healthy patient having the same height, weight, age and sex as the patient being treated, by accessing a look up table in the patient profile stored locally on the system memory or in a remote database. A normal range for pH in arterial blood is 7.35-7.45 at 37 degrees Celsius. The processor receives a signal from the sensor measuring arterial pH in the blood circuit, which indicates a value for the sensed arterial pH in the blood during treatment 352. The processor selects an average value of the normal range of values for arterial pH in a healthy patient as the target value 354. The processor compares the measured pH value to the target value 356. The processor controls the fluid flow regulator, e.g., an infusion pump, which is in fluid communication with the blood carrying conduit of the extracorporeal circulatory support system, to pump an alkaline drug, e.g., bicarbonate or an acidic drug, e.g., sodium or potassium, into the blood circuit until the measured arterial pH reaches the target value 358. Optionally, the system may prompt the caregiver to approve infusion or delivery of the drug into the blood circuit based on the target value prior to the infusion or delivery taking place. The processor continues to receive signals from the sensor measuring arterial pH in the blood circuit. Once the target value is reached, the processor will cause the infusion pump to add bicarbonate or sodium potassium to the blood circuit as needed to maintain the target pH level in the patient based on feedback from the atrial pH sensors.

Figure 6:
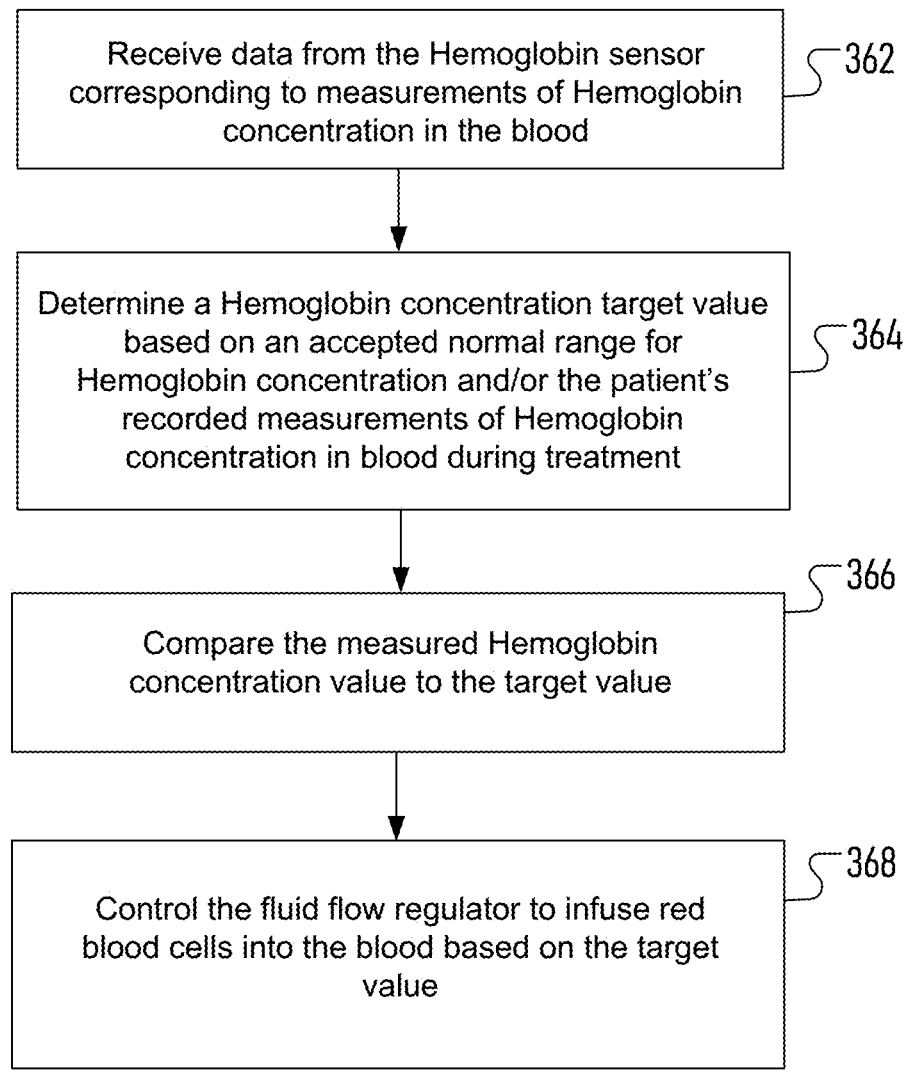
FIG. 6 shows a flow diagram of a system for controlling infusion of one or more supplements into blood received from a patient based on Hemoglobin measurement.

FIG. 6 shows a fourth example of a flow diagram of a system for controlling infusion or delivery of one or more supplements into blood received from a patient. The system includes a Hemoglobin sensor, e.g., a sensor utilizing optical reflectance technology for measuring Hemoglobin concentration in the patient's arterial or venous blood, for example, such as the technology used with the H/S cuvette provided by Terumo. The system can be implemented via the control system 120 of FIG. 1 or FIG. 13 using the processor and memory storage device to execute various actions. The processor is configured to perform the following steps: The processor retrieves a normal range of values for venous Hemoglobin concentration in a healthy patient having the same height, weight, age and sex as the patient being treated, by accessing a look up table in the patient profile stored locally on the system memory or in a remote database. A normal range for venous Hemoglobin concentration is 14.0 to 18.0 grams per deciliter for males and 12 to 16 grams per deciliter for females. The processor receives a signal from the sensor measuring venous Hemoglobin concentration in the blood circuit, which indicates a value for the sensed venous Hemoglobin concentration in the blood during treatment 362. The processor selects an average value of the normal range of values for venous Hemoglobin concentration in a healthy patient as the target value 364. The processor compares the measured Hemoglobin concentration value to the target value 366. The processor controls the fluid flow regulator, e.g., an infusion pump, which is in fluid communication with the blood carrying conduit of the extracorporeal circulatory support system, to pump red blood cells into the blood circuit until the measured venous Hemoglobin concentration reaches the target value 368. Optionally, the system may prompt the caregiver to approve infusion or delivery of red blood cells into the blood circuit based on the target value prior to the infusion or delivery taking place. The processor continues to receive signals from the sensor measuring venous Hemoglobin concentration in the blood circuit. Once the target value is reached, the processor will cause the infusion pump to infuse red blood cells into the blood circuit as needed to maintain the target venous Hemoglobin concentration in the patient based on feedback from the venous Hemoglobin sensors.

Figure 7:
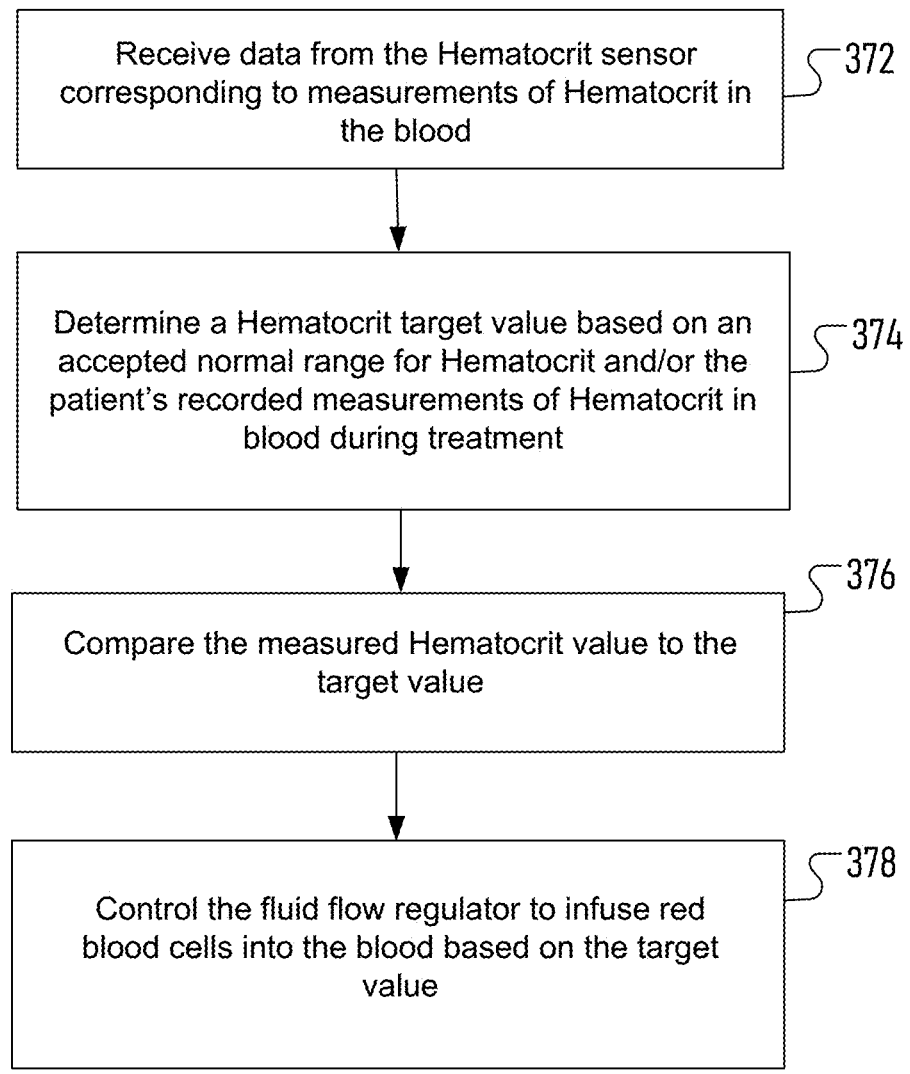
FIG. 7 shows a flow diagram of a system for controlling infusion of one or more supplements into blood received from a patient based on Hematocrit measurement.

FIG. 7 shows a fifth example of a flow diagram of a system for controlling infusion or delivery of one or more supplements into blood received from a patient. The system includes a Hematocrit sensor, e.g., a sensor utilizing optical reflectance technology for measuring a patient's Hematocrit, i.e., the volume percentage of red blood cells in arterial or venous blood, for example, such as the technology used with the H/S cuvette provided by Terumo. The system can be implemented via the control system 120 of FIG. 1 or FIG. 13 using the processor and memory storage device to execute various actions. The processor is configured to perform the following steps: The processor retrieves a normal range of values for venous Hematocrit in a healthy patient having the same height, weight, age and sex as the patient being treated, by accessing a look up table in the patient profile stored locally on the system memory or in a remote database. A normal range for venous Hematocrit is 35.5 to 44.9 percent for females and 38.3 to 48.6 percent for males. The processor receives a signal from the sensor measuring venous Hematocrit in the blood circuit, which indicates a value for the sensed venous Hematocrit in the blood during treatment 372. The processor selects an average value of the normal range of values for venous Hematocrit concentration in a healthy patient as the target value 374. The processor compares the measured Hematocrit value to the target value 376. The processor controls the fluid flow regulator, e.g., an infusion pump, which is in fluid communication with the blood carrying conduit of the extracorporeal circulatory support system, to pump red blood cells into the blood circuit until the measured venous Hematocrit reaches the target value 378. Optionally, the system may prompt the caregiver to approve infusion or delivery of red blood cells into the blood circuit based on the target value prior to the infusion or delivery taking place. The processor continues to receive signals from the sensor measuring venous Hematocrit in the blood circuit. Once the target value is reached, the processor will cause the infusion pump to infuse red blood cells into the blood circuit as needed to maintain the target venous Hematocrit in the patient based on feedback from the venous Hematocrit sensors.

Figure 8:
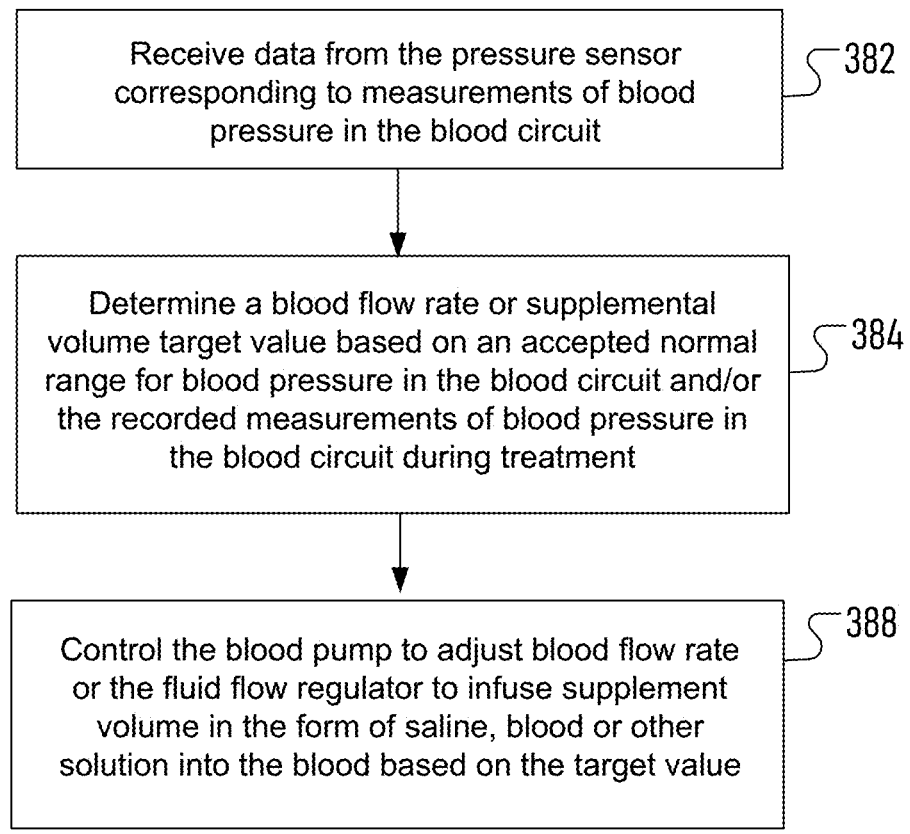
FIG. 8 shows a flow diagram of a system for controlling blood parameters in an extracorporeal blood circuit based on a blood pressure measurement.

FIG. 8 shows an example of a flow diagram of a system for controlling blood parameters in an extracorporeal blood circuit. The system includes a pressure sensor for measuring the arterial pressure of blood in the blood circuit. The pressure sensor may include an electronic pressure transducer e.g., a piezoresistive pressure sensor. The pressure sensor may be located in one or more of the following locations, e.g., outlet of the blood pump, outlet of the oxygenator or other locations in the blood circuit or system. The system can be implemented via the control system 120 of FIG. 1 or FIG. 13 using the processor and memory storage device to execute various actions. The processor is configured to perform the following steps: The processor retrieves a normal range of values for arterial blood pressure in a healthy patient having the same height, weight, age and sex as the patient being treated, by accessing a look up table in the patient profile stored locally on the system memory or in a remote database. An accepted normal range for arterial blood pressure in the blood circuit is 250 mmHg to 400 mmHg at the outlet of the blood pump, or 50 mmHg to 200 mmHg at the outlet of the oxygenator. The processor receives a signal from the sensor measuring arterial blood pressure in the blood circuit, which indicates a value for the sensed arterial blood pressure in the blood during treatment 382. The processor calculates the delta between the average value in the normal range of values for arterial blood pressure and the received value for the sensed arterial blood pressure of the patient during treatment. The processor determines the target value for the flow rate of the blood or for the volume of supplement (e.g., saline solution) to be added to the blood circuit using a standard PID algorithm (see above) and the calculated delta value 384. The processor controls the arterial blood pump in the blood circuit to adjust the flow rate of blood pumped through the blood circuit based on a target value or it causes the infusion pump to infuse or deliver solution into the blood circuit based on target value 388, e.g., to adjust and/or maintain arterial blood pressure.

Figure 9:
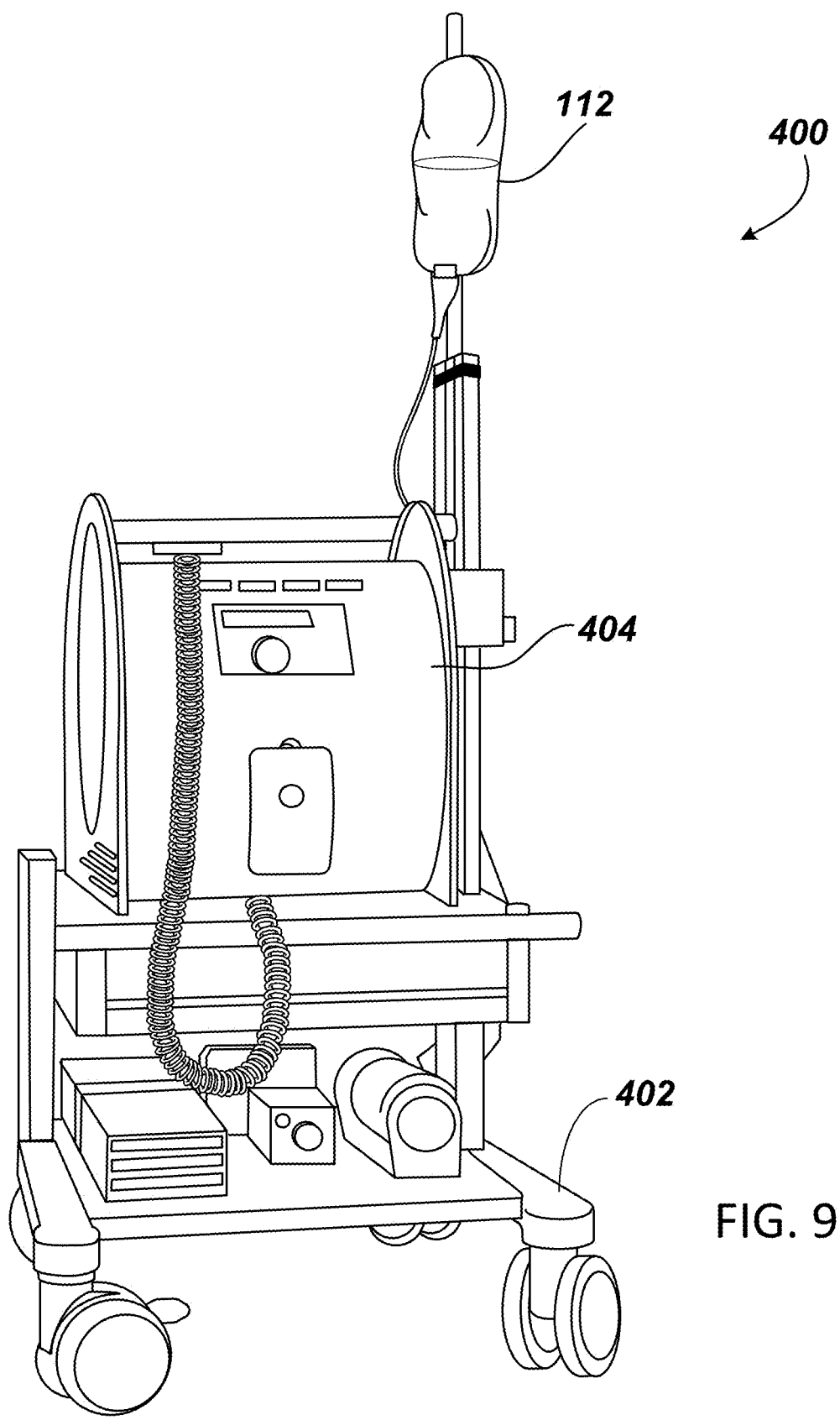
FIG. 9 is a perspective view of an extracorporeal membrane oxygenation machine (ECMO).

FIG. 9 illustrates a perspective view of an extracorporeal membrane oxygenation machine (ECMO) 400 that can be implemented with one or more of the particular embodiments described herein. The ECMO machine is provided with a mobile platform 402 and includes the supplemental container 112 positioned on a pole for gravity feeding into the blood reservoir 108 and opening of valve 110 via control system 120. The pumping and oxygenation components of the ECMO machine 400 are positioned in the housing 404.

Figure 10:
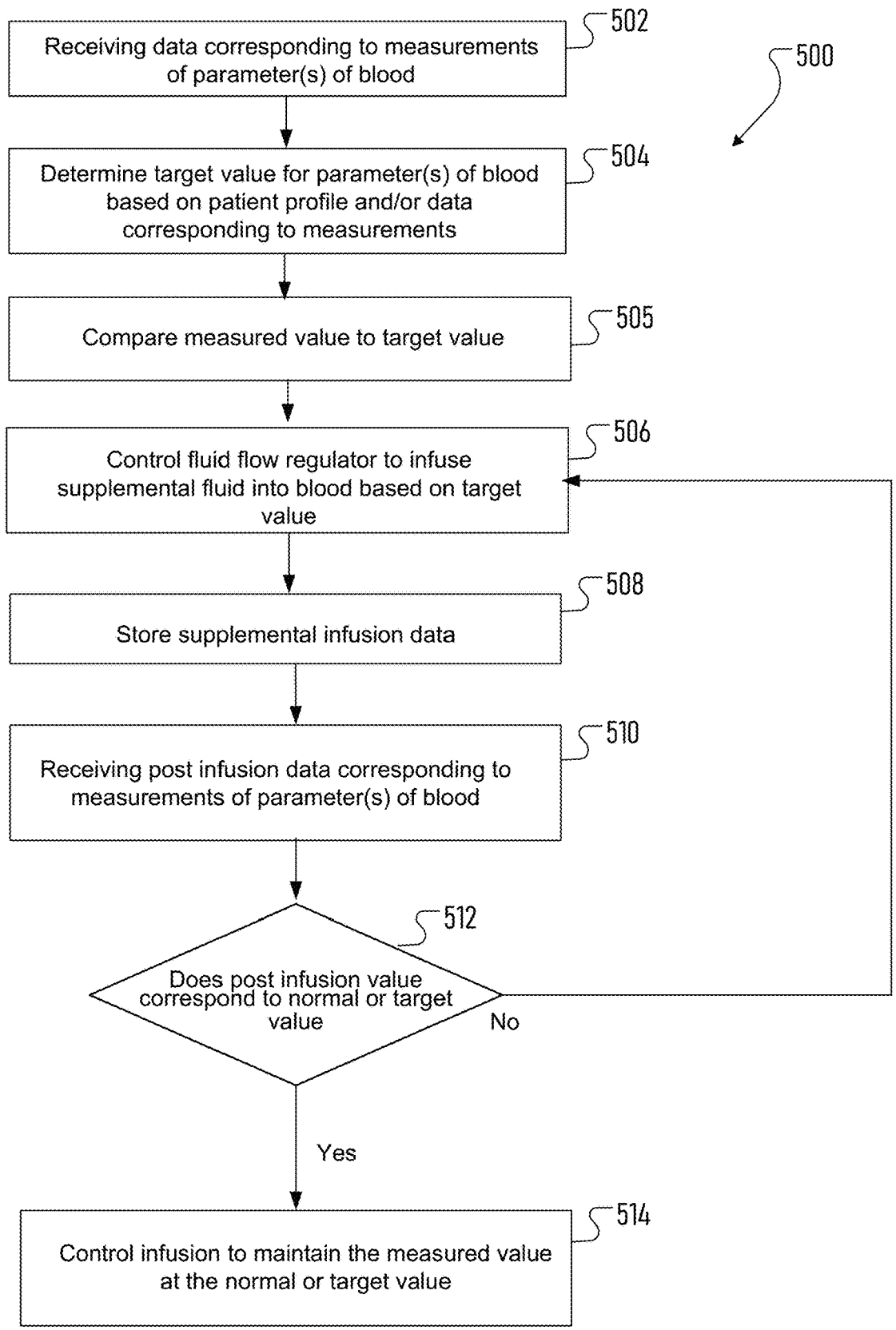
FIGS. 10-11G show flow diagrams of systems for controlling infusion of one or more supplements into blood received from a patient and/or for controlling blood parameters in an extracorporeal blood circuit.
Figure 11A:
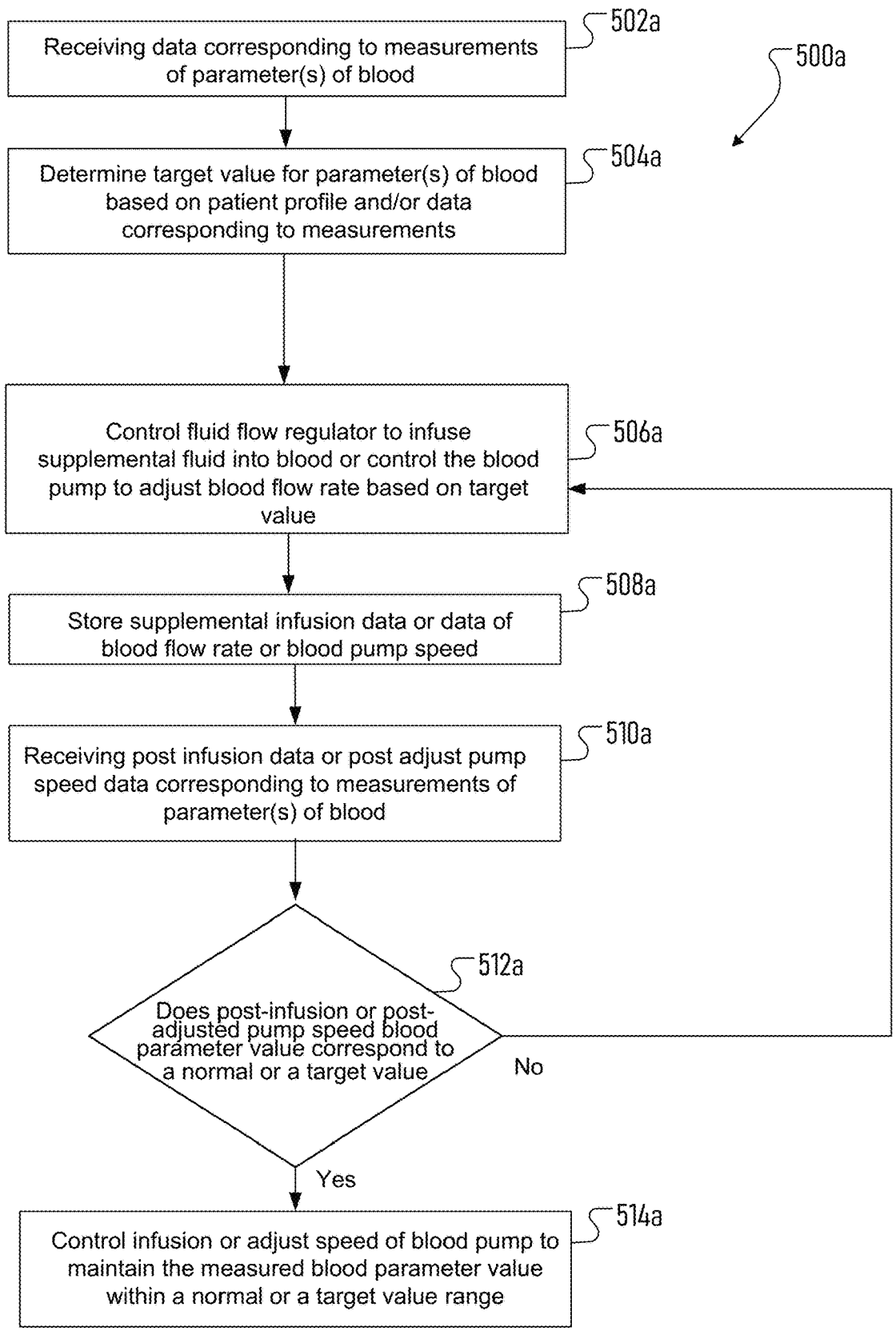

FIG. 10 shows a flow diagram of a system for controlling infusion of one or more supplements into blood received from a patient. FIG. 11A shows a flow diagram of a system for controlling infusion of one or more supplements into blood received from a patient or controlling blood pump speed. FIGS. 11A-11G show examples of how a system can be implemented for controlling infusion or pump speed based on the specific measured properties and/or accepted normal range of properties stored in a patient profile as discussed in connection with FIGS. 3-8, respectively. The system 500 can be implemented via the control system 120 of FIG. 1 or FIG. 13 using the processor and memory storage device to execute various actions. At 502, the control system 120 receives data corresponding to measurements of parameter(s) of blood, e.g., such as any of the parameters described herein. The parameters are obtained from one or more sensors (e.g., sensor(s) 106, 729), e.g., such as any of the various sensors described herein. At 504, the control system 120 determines a target value for the parameter(s) of blood. This target value can be based on a patient profile and/or data corresponding to measurements of the one or more sensors 106. At 505, the control system 120 may compare the measured value to the target value. At 506, the control system 120 controls a fluid flow regulator (such as, valve 110 or an infusion pump) to infuse supplemental fluid into blood based on the target value and/or based on a difference in the measured value and the target value. At 508, the control system 120 stores data about the infusion (e.g., quantity, time, administration period) on the memory device. The information about the infusion can be stored in the patient profile or can be used to generate a new patient record. The information about the infusion can also be presented on a display device or user interface of the control system 120 for review by a physician, nurse, or administrator. At 510, the control system 120 receives post infusion data corresponding to measurements of parameters of the blood post infusion. The infusion data can be obtained via one or more of the various sensors described herein. The control system 120 analyzes the parameters of the blood post infusion with respect to the target values at 512. If the values are within range or within normal range, then the system 120 will stop infusion into the circuit at 514, reduce the rate of infusion, or maintain a regulated rate of infusion in order to maintain the blood parameters within the normal or target value range or at a normal or target value. If the measured values are determined at 512 to fall outside the normal or target value or normal or target value range, the control system 120 initiates further infusion or provides continuous infusion of supplemental fluids at 506. Accordingly, the control system 120 provides a feedback control loop system for measuring, infusing, and re-measuring and re-infusing as necessary. Both the cumulative and current totals of fluids added can be reported and retained in an administration record or data log for the patient, patient profile, or heath record. Furthermore, because the data may be targeted for patient specific parameters or accepted patient norms, and/or based on real-time measurements, the system can be operated without the need for a highly skilled operator.

FIG. 11A shows a flow diagram of a system for controlling infusion of one or more supplements into blood received from a patient or controlling blood pump speed. The system 500 can be implemented via the control system 120 of FIG. 1 or FIG. 13 using the processor and memory storage device to execute various actions. At 502a, the control system 120 receives data corresponding to measurements of parameter(s) of blood, e.g., such as any of the parameters described herein. The parameters are obtained from one or more sensors (e.g., sensor(s) 106, 729), e.g., such as any of the various sensors described herein. At 504a, the control system 120 determines a target value for the parameter(s) of blood or fluid to be unfused. This target value can be based on a patient profile and/or data corresponding to measurements of the one or more sensors 106. At 506a, the control system 120 controls a fluid flow regulator (such as, valve 110 or an infusion pump) to infuse supplemental fluid into blood or controls the blood pump, e.g., to adjust blood flow rate, based on the target value and/or based on a difference in the measured value and the target value. At 508*a*, the control system 120 stores data about the infusion (e.g., quantity, time, and administration period) or data of blood flow rate or blood pump speed on the memory device. The data can be stored in the patient profile or can be used to generate a new patient record. The data can also be presented on a display device or user interface of the control system 120 for review by a physician, nurse, or administrator. At 510*a*, the control system 120 receives post infusion data or post adjusted pump speed data corresponding to measurements of parameters of the blood. The infusion data or adjusted pump speed data can be obtained via one or more of the various sensors described herein. The control system 120 analyzes the parameters of the blood post infusion or post adjusted pump speed with respect to normal or target values at 512*a*. If the values are within range or within normal range, then the system 120 will stop infusion into the circuit at 514*a*, reduce the rate of infusion, maintain a regulated rate of infusion or maintain a regulated rate of pump speed in order to maintain the blood parameters within a normal or target value range or at a normal or target value. If the measured values are determined at 512*a* to fall outside the normal or target value or normal or target value range, the control system 120 initiates further infusion, provides continuous infusion of supplemental fluids at 506*a* or further adjusts the blood pump speed and/or blood flow rate. Accordingly, the control system 120 provides a feedback control loop system for measuring, infusing or adjusting pump speed, and re-measuring and re-infusing or re-adjusting pump speed as necessary. Both the cumulative and current totals of fluids added can be reported and retained in an administration record or data log for the patient, patient profile, or heath record. Furthermore, because the data may be targeted for patient specific parameters or accepted patient norms, and/or based on real-time measurements, the system can be operated without the need for a highly skilled operator.

Figure 11B:
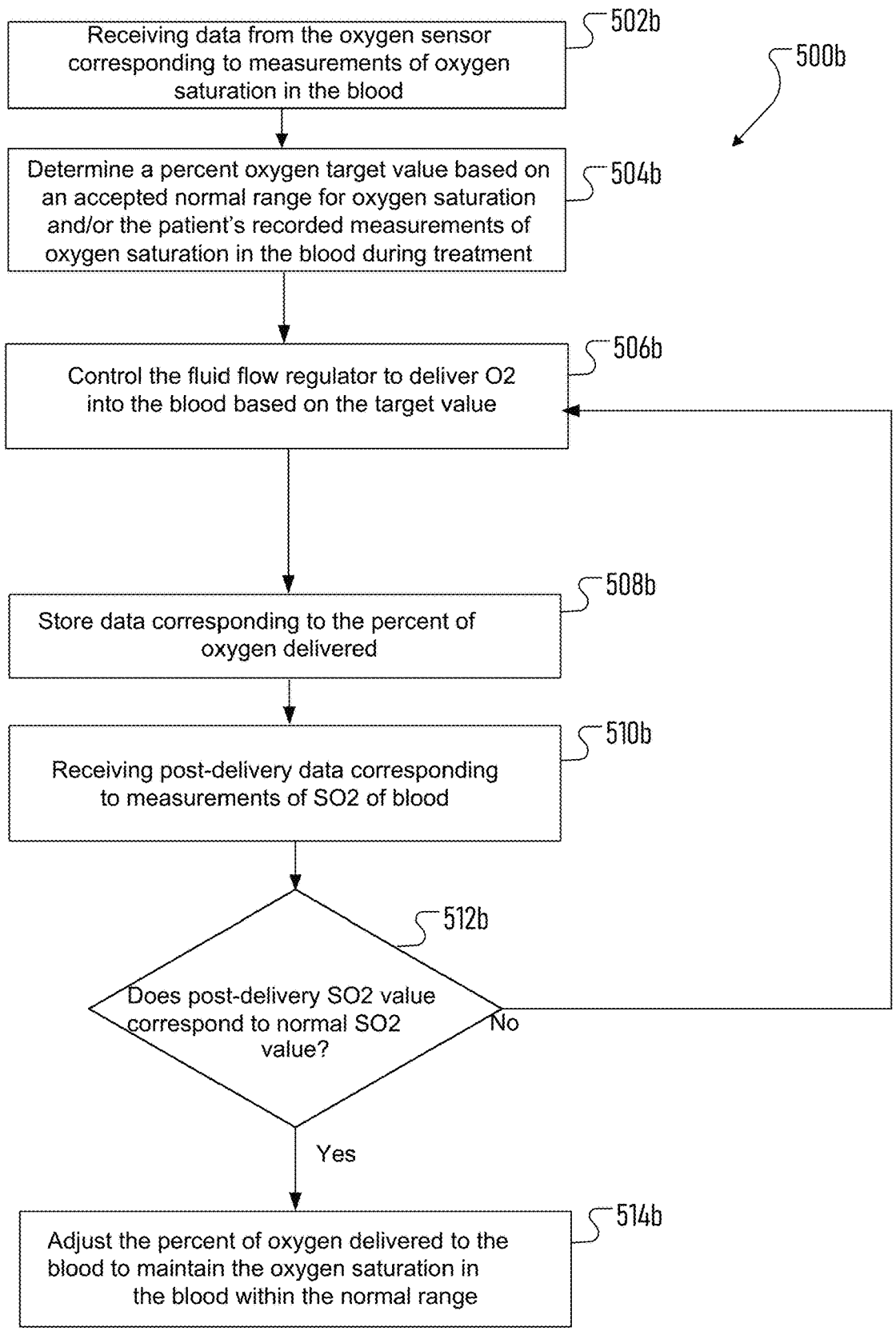

FIG. 11B shows a flow diagram of a system for controlling infusion into blood received from a patient based on SO2 measurements, as described in FIG. 3. Steps 502*b*-506*b* of system 500*b* correspond to 302-308 of FIG. 3. As demonstrated in FIG. 11B, at 508*b* system 500*b* stores data corresponding to the percent of oxygen gas delivered to the blood. System 500*b* receives post infusion or delivery data at 510*b* corresponding to SO2 measurements taken of the patient's blood post infusion or delivery. The control system 120 analyzes the parameters of the blood post infusion or delivery with respect to SO2 at 512*b*. If the measured SO2 values are within normal range, then the system 120 will adjust the percent of oxygen gas delivered to the blood in order to maintain the oxygen saturation in the blood within the normal range.

Figure 11C:
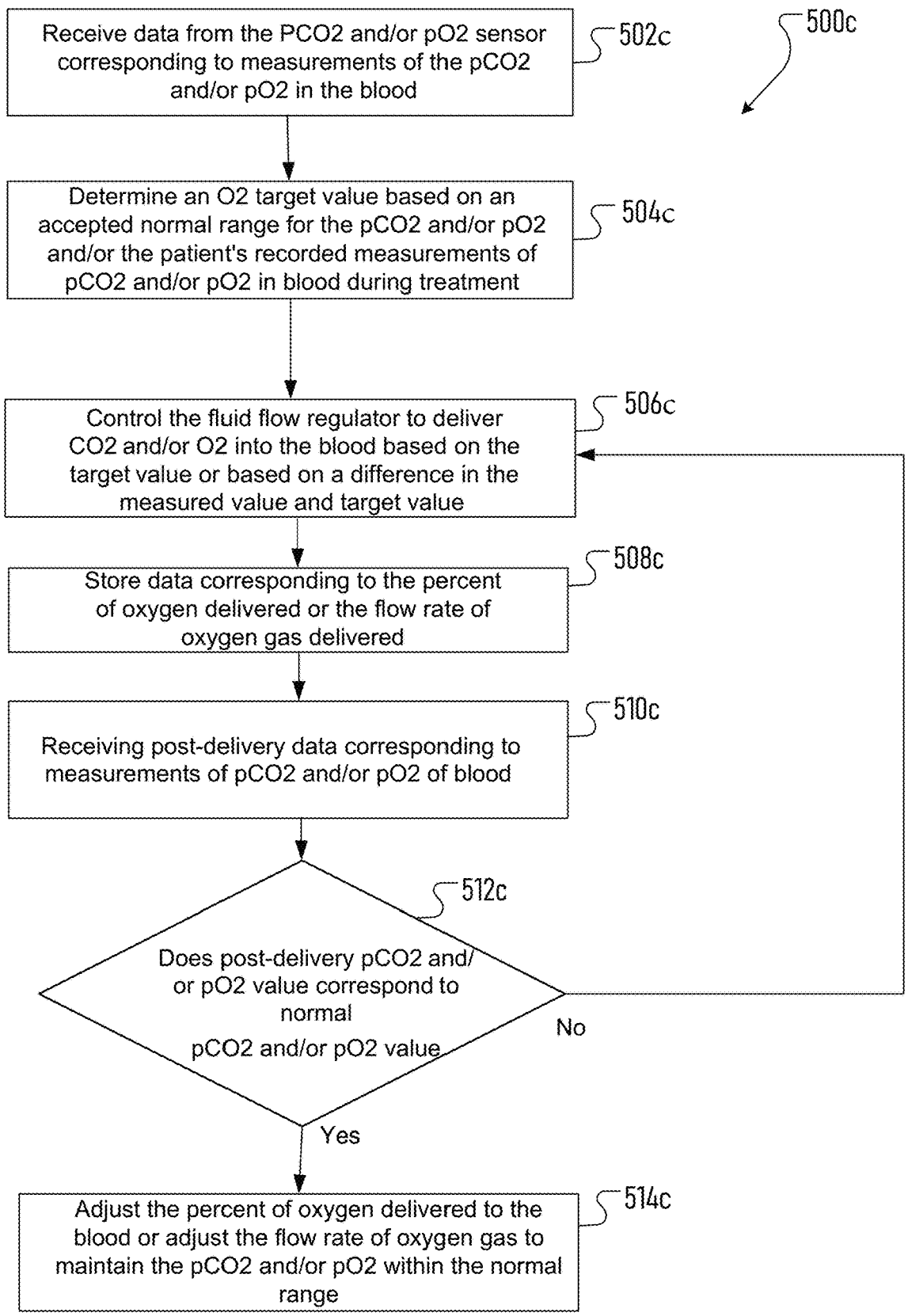

FIG. 11C shows a flow diagram of a system for controlling infusion into blood received from a patient based on pCO2 and/or pO2 measurements, as described in FIG. 4. Steps 502*c*-506*c* of system 500*c* correspond to 342-348 of FIG. 4. As demonstrated in FIG. 11C, at 508*c* system 500*c* stores supplemental data corresponding to the percent of oxygen gas delivered to the blood or the flow rate of oxygen gas delivered to the blood. System 500*c* receives post infusion or delivery data at 510*c* corresponding to pCO2 and/or pO2 measurements taken of the patient's blood post infusion or delivery. The control system 120 analyzes the parameters of the blood post infusion or delivery with respect to pCO2 and/or pO2 at 512*c*. If the measured pCO2 and/or pO2 value(s) are within normal range, then the system 120 will adjust the percent of oxygen gas delivered to the blood or adjust the flow rate of oxygen gas delivered to the blood in order to maintain the pCO2 and/or pO2 parameter(s) within the normal range.

Figure 11D:
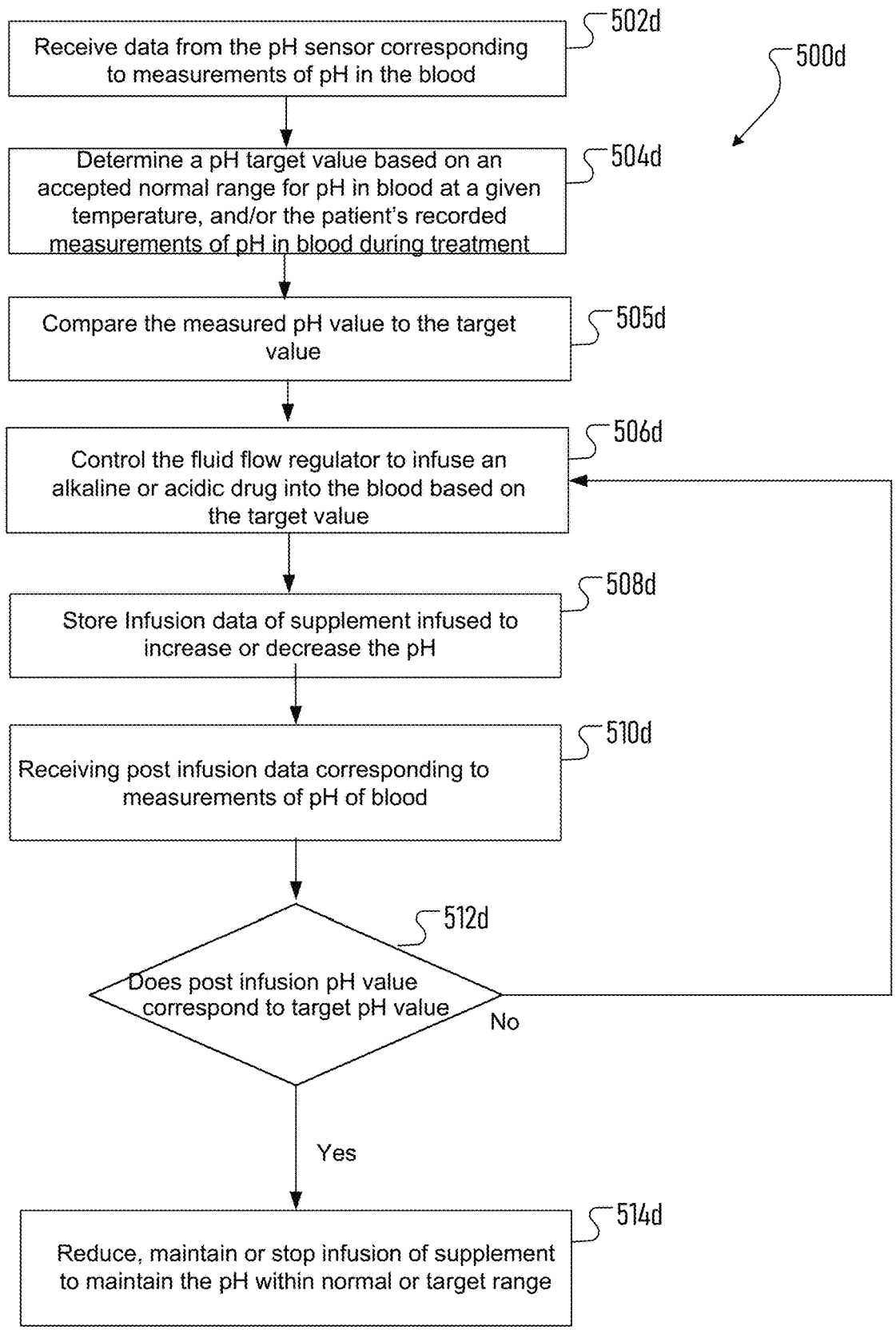

FIG. 11D shows a flow diagram of a system for controlling infusion into blood received from a patient based on pH measurements, as described in FIG. 5. Steps 502*d*-506*d* of system 500*d* correspond to 352-358 of FIG. 5. As demonstrated in FIG. 11D, at 508*d* system 500*d* stores supplemental data corresponding to infusion quantities of a supplement effective to increase or decrease the pH in the patient's blood. System 500*d* receives post infusion data at 510*d* corresponding to pH measurements taken of the patient's blood post infusion. The control system 120 analyzes the parameters of the blood post infusion with respect to the pH at 512*d*. If the measured pH value is at the target value, then the system 120 will cease infusion of the supplement (alkaline or acidic drug) into the circuit at 514*d*, reduce the rate of infusion, or maintain a regulated rate of infusion of the supplement in order to maintain the pH parameter(s) within the normal range.

Figure 11E:
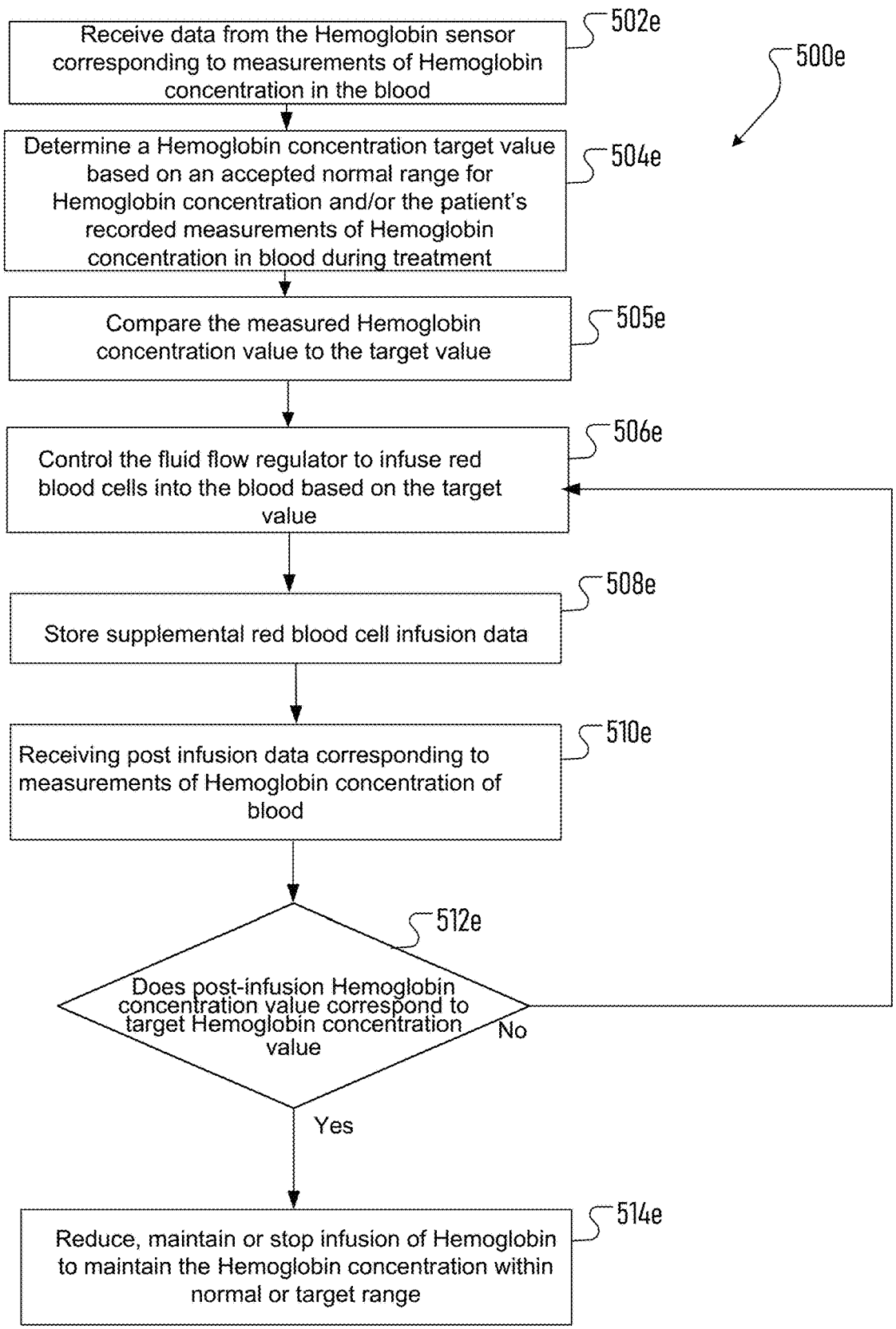

FIG. 11E shows a flow diagram of a system for controlling infusion into blood received from a patient based on Hemoglobin concentration measurements, as described in FIG. 6. Steps 502*e*-506*e* of system 500*e* correspond to 362-368 of FIG. 6. As demonstrated in FIG. 11E, at 508*e* system 500*e* stores supplemental data corresponding to infusion quantities of red blood cells infused into the patient's blood. System 500*e* receives post infusion data at 510*e* corresponding to Hemoglobin concentration measurements taken of the patient's blood post infusion. The control system 120 analyzes the parameters of the blood post infusion with respect to the target values of Hemoglobin concentration at 512*e*. If the measured Hemoglobin concentration value is at the target value, then the system 120 will cease infusion of red blood cells into the circuit at 514*e*, reduce the rate of red blood cell infusion, or maintain a regulated rate of red blood cell infusion in order to maintain the Hemoglobin concentration within the normal range.

Figure 11F:
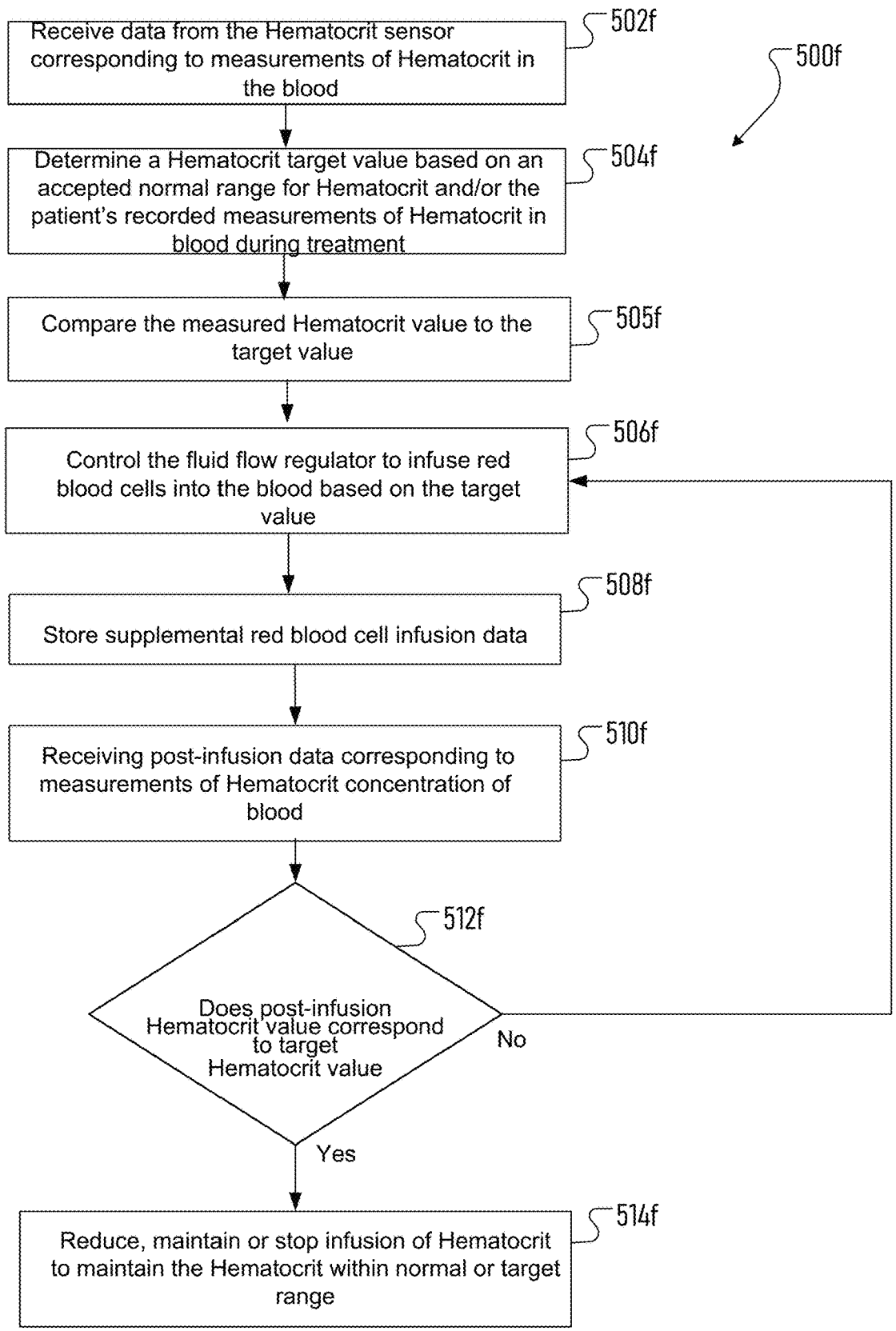

FIG. 11F shows a flow diagram of a system for controlling infusion into blood received from a patient based on Hematocrit concentration measurement as described in FIG. 7. Steps 502*f*-506*f* of system 500*f* correspond to 372-378 of FIG. 7. As demonstrated in FIG. 11F, at 508*f* system 500*f* stores supplemental data corresponding to infusion quantities of red blood cells infused into the patient's blood. System 500*f* receives post infusion data at 510*f* corresponding to Hematocrit concentration measurements taken of the patient's blood post infusion. The control system 120 analyzes the parameters of the blood post infusion with respect to the target values of Hematocrit concentration at 512*f* If the measured Hematocrit concentration value is at the target value, then the system 120 will cease infusion of red blood cells into the circuit at 514*f*, reduce the rate of red blood cell infusion, or maintain a regulated rate of red blood cell infusion in order to maintain the Hematocrit within the normal range.

Figure 11G:
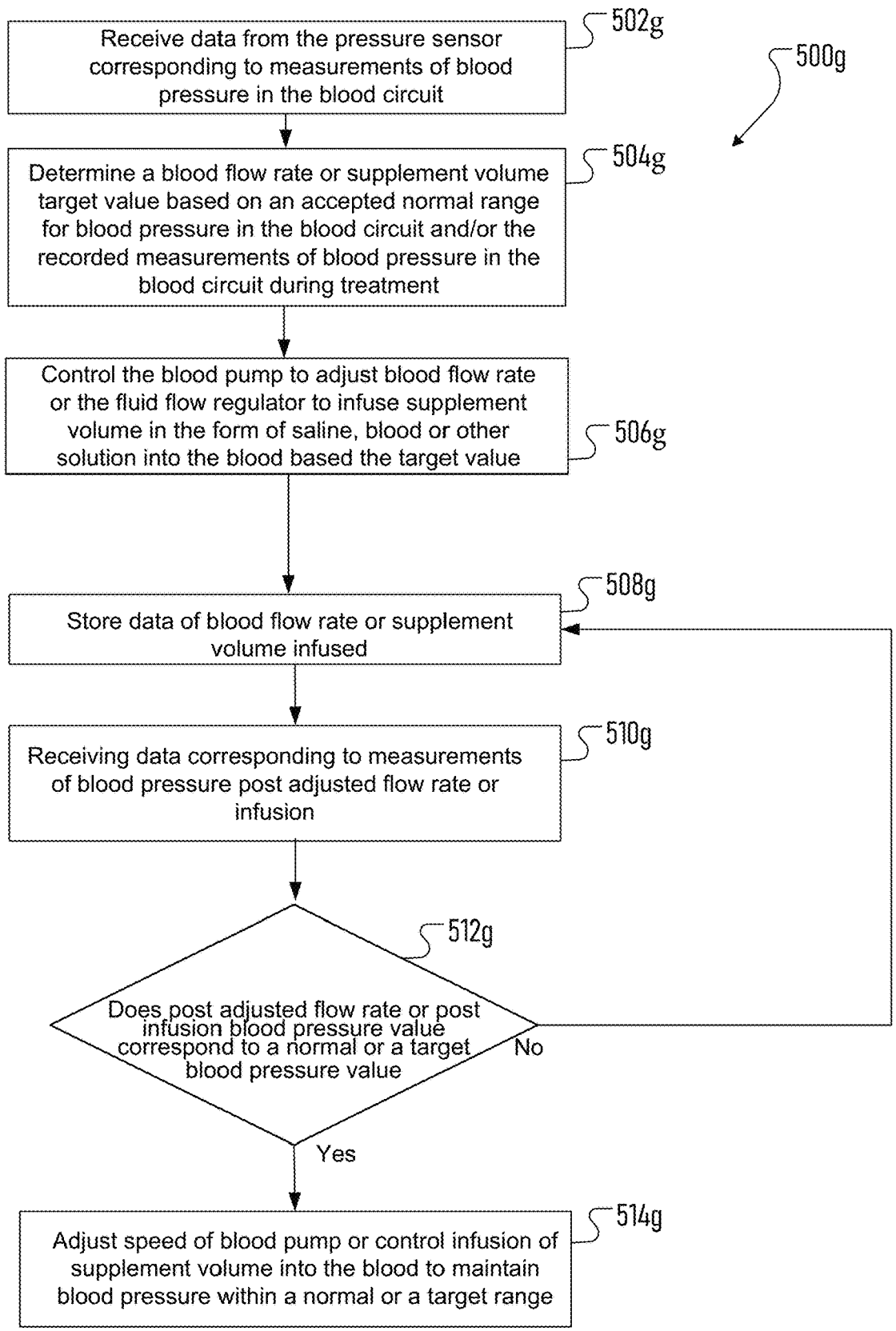

FIG. 11G shows a flow diagram of a system for controlling parameters of blood received from a patient based on blood pressure measurements as described in FIG. 8. Steps 502*g*-506*g* of system 500*g* correspond to 382-388 of FIG. 8. As demonstrated in FIG. 11G, at 508*g* system 500*g* stores data corresponding blood flow rate or infusion volume of saline, blood or other solution infused into the patient's blood. System 500*g* receives data at 510*g* corresponding to blood pressure measurements taken of the patient's blood post adjusted rate or post infusion. The control system 120 analyzes the parameters of the blood post adjusted rate or post infusion with respect to the normal or target values of blood pressure at 512g. If the measured blood pressure is within range, then the system 120 will cease infusion of saline, blood or other solution into the blood circuit at 514g, or maintain a regulated rate of infusion of saline, blood or other solution into the blood in order to maintain the blood pressure within the normal range or adjust the speed of the blood pump to maintain the blood pressure within the normal range.

Figure 12:
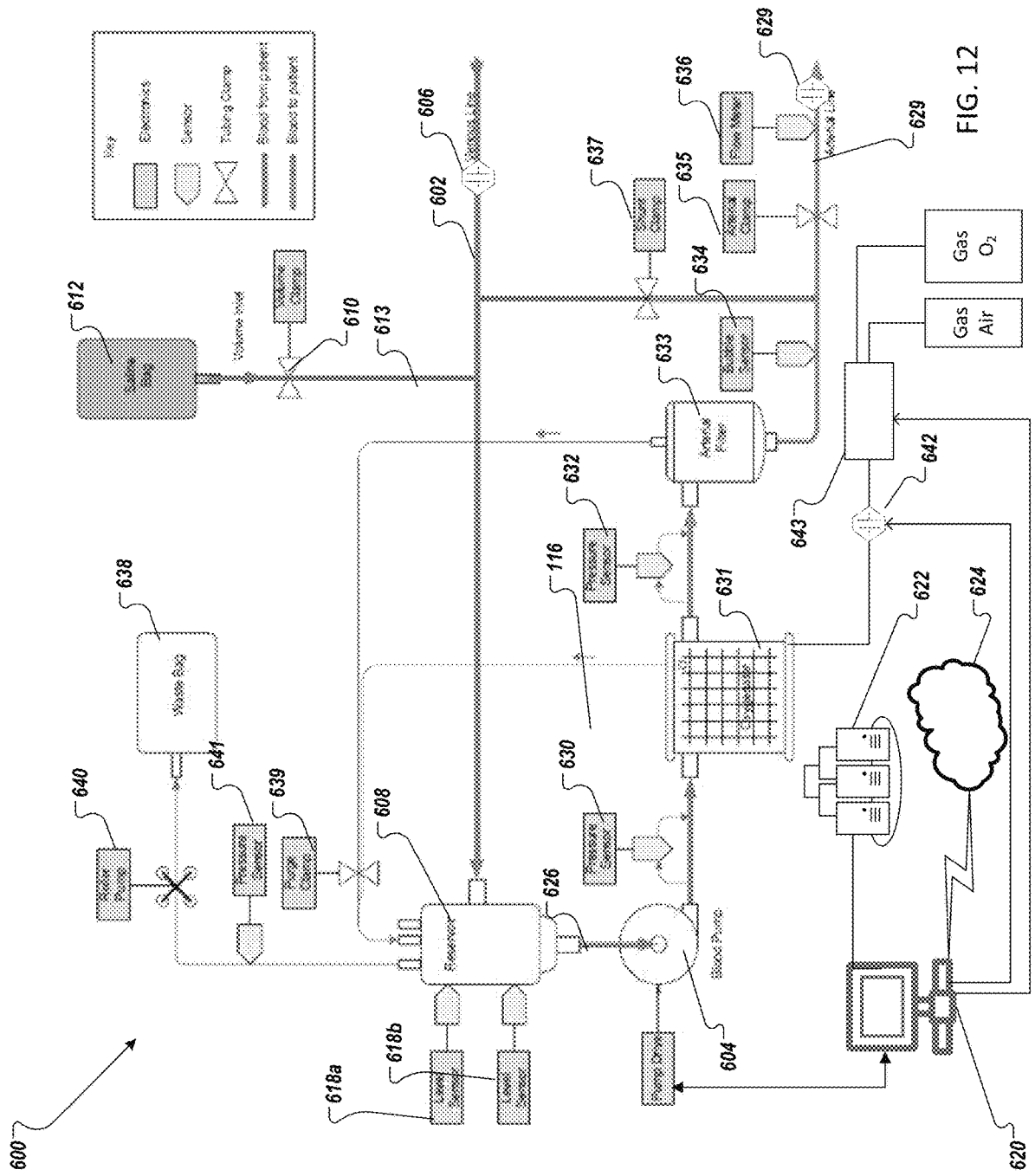
FIG. 12 is a schematic diagram of an ECMO system for controlling infusion or delivery of one or more supplements into blood received from a patient.

FIG. 12 is a schematic diagram of an ECMO system capable of controlling infusion of one or more supplements into blood received from a patient and/or capable of controlling blood parameters in an extracorporeal blood circuit, e.g., by regulating blood pump speed. The system 600 receives blood from a patient via a venous line 602. One or more sensors 606, 629 is fluidly coupled to the venous line 602 or arterial line 629 to detect a property of the blood being received from the patient. The sensor(s) 606, 629 can measure parameters such as oxygen, flow rate, pressure, hemoglobin content, hematocrit content, pH, CO2 level, and/or temperature. The sensor(s) 606, 629 is communicably coupled to a control system 620. The control system 620 includes a processor, a memory (either local or remote), and associated circuitry for controlling flow of the blood and/or infusion of one or more supplemental constituents into the blood received from the patient pursuant to a processor-readable computer program providing a set of instructions stored on the memory device and based on the state of the blood. The blood received from the patient may be pumped to a blood reservoir 608. The blood reservoir includes sensors 618a and 618b for measuring a level of fluid in the blood reservoir. In certain implementations, the system 600 may not include a reservoir and one or more of the sensors may be positioned along the venous line and/or the arterial line, or elsewhere in the system.

The system 600 includes a supplemental reservoir e.g., a saline bag 112 containing saline for infusion into the blood received from the patient and contained in the reservoir 608. While a saline bag is shown in FIG. 12, other implementations of system 600 may include supplemental reservoirs or bags filled with one or more other supplements. For example, one or more supplemental reservoirs may be fluidly coupled to the venous line 602 for infusion of supplements such as blood, and/or medication into the blood received from the patient. The saline bag 612 is fluidly coupled to the venous line 602 via a fluid conduit 613. A volume clamp 610, may be communicably coupled (wired or wirelessly) to the control systems 620 and may be controlled (fully or partially opened or closed) to permit transmission of the saline or other fluid from supplemental reservoir 612. One or more sensors can be positioned along the fluid conduit 613 for sensing properties such as pressure, flow rate, duration run, quantity, or other parameters of the supplemental fluid obtained from the supplemental reservoir 612. In some implementations, an active component such as an infusion pump or a fluid source clamp may be used in place of or in concert with the valve 610 for actively pumping the supplemental fluid from the supplemental reservoir 612. The infusion pump can also be communicably coupled to the control system 620.

The system 600 may include an oxygenator 631 fluidly coupled to the blood circuit and configured to provide oxygen to the blood from the patient. Pressure sensors 630 and 632 may be positioned upstream and downstream of the oxygenator 631. The system may also include an arterial filter 633 and a bubble sensor 634 for sensing parameters of the blood post oxygenation. A purge clamp may be positioned downstream of the blood reservoir. The bubble sensor and pressure sensors are also communicably coupled to the control system 620. The system may also include a waste bag 638 and a pressure sensor 641 and pump 640 fluidly coupling the waste bag 638 to blood reservoir 608. An arterial clamp 635 may be positioned on the arterial line 628 for assisting with controlling of flow from the ECMO system back to the patient. A flow meter 636 may also be positioned on the arterial line 628. Both the flow meter 636 and the arterial clamp 635 are communicably coupled to the control system 620. An arterial line sensor 629 may also positioned on the arterial line 628 for measuring content of the blood flowing back to the patient. The system may include a fluid flow regulator, e.g., a needle valve 642, which controls the flow of oxygen gas into the blood circuit, to adjust the flow rate of oxygen gas delivered to or infused into the blood circuit (via the oxygenator). The system may include a fluid flow regulator, e.g., an electronic gas blender 643 (which is in fluid communication with the blood carrying conduit and/or an oxygenator of the extracorporeal circulatory support system) to adjust the percentage of oxygen gas delivered to or infused into the blood circuit (via an oxygenator).

The control system 620 controls the oxygenation of blood, blood flow rate, and also controls the infusion of blood pumped into the system 600 with supplemental fluids such as saline. The system 600 is communicably coupled to a database either locally (for example on server 622) or remotely via network 624. The control system 620 controls the infusion and oxygenation of blood entering the system 600 based on a target value for parameters of the blood, which target value is based on parameters of the blood sensed via sensor 606, 629 and/or based on data about the patient or acceptable or normal values for blood parameters for patients having certain biometrics stored in a patient profile, stored on a memory device and accessible via control system 620. The control system 620 controls infusion or flow rate of the blood entering the system to bridge the gap between the target value for one or more parameters of the blood and the measured values of the blood. The control system 620 retains a log of the infusions, flow rate, and other parameters and monitors the measured values and trends.

Figure 13:
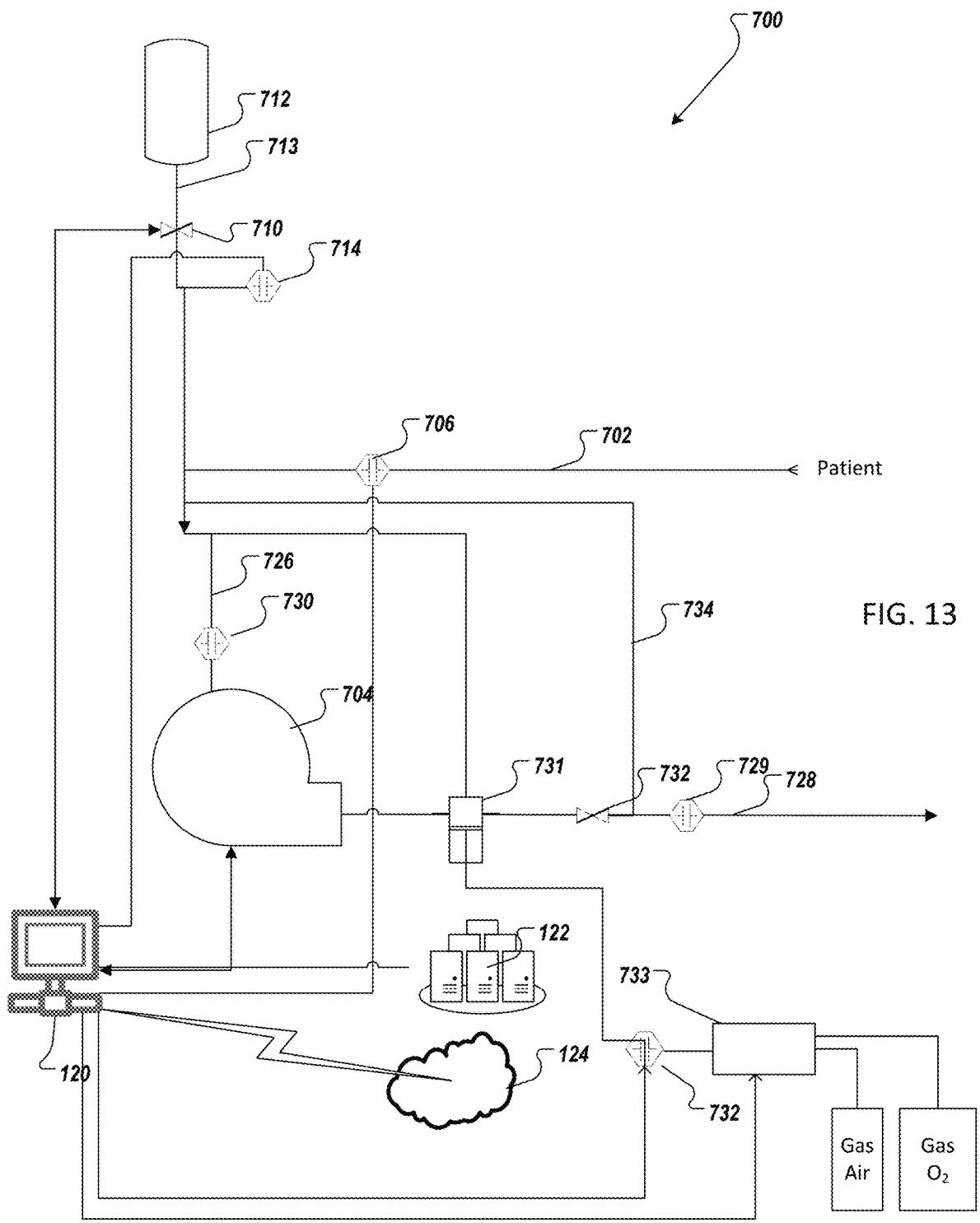
FIG. 13 is a schematic diagram of another system for controlling infusion or delivery of one or more supplements into blood received from a patient.

FIG. 13 is a schematic diagram of another system capable of controlling infusion of one or more supplements into blood received from a patient and/or capable of controlling blood parameters, e.g., blood flow, in an extracorporeal blood circuit, e.g., by regulating blood pump speed. The system 700 receives blood from a patient via a venous line 702. One or more sensors 706, 729 is fluidly coupled to the venous line 702 or the arterial line 728 to detect a property of the blood being received from the patient. The sensor(s) 706, 728 can measure parameters such as oxygen, flow rate, pressure, hemoglobin content, hematocrit content, pH, CO2 level, and/or temperature. The sensor(s) 706, 728 is communicably coupled to a control system 720. The control system 720 includes a processor, a memory, and associated circuitry for controlling flow of the blood and/or infusion of one or more supplemental constituents into the blood received from the patient pursuant to a processor-readable computer program providing a set of instructions stored on a memory device (either local or remote) and based on the state of the blood. Pump 704 provides a pressure differential over venous line 702 and also over supplemental line 713 in response to supplement valve 710 being opened so that one or more supplemental reservoirs, containers or other supplemental fluid source 712 are infused into the blood received from the patient. The supplements 712 can include supplemental fluids such as blood, saline, medication or other fluids. The implementations including multiple supplemental fluids may include multiple containers containing each of the fluids, or a single container with multiple chambers for keeping different supplemental fluids separate, which may be independently added or infused into the patient blood in the extracorporeal blood circuit. The valve 710 is communicably coupled to the control systems 720 and can be controlled (fully or partially opened or closed) to permit transmission of a supplemental fluid from supplemental reservoir 712 into the venous line 713. One or more sensors 714 can be positioned along the fluid conduit 713 for sensing properties such as pressure, flow rate, duration run, quantity, or other parameters of the supplemental obtained from the supplemental container 712. In some implementations, an active component such as an infusion pump or a fluid source clamp may be used in place of or in concert with the valve 710 for actively pumping the supplemental fluid from the supplemental container 712. The infusion pump can also be communicably coupled to the control system 720.

The control system 720 controls the flow of the supplemental fluid from the supplemental container 712 based, at least in part, on the content and/or state of the blood in the extracorporeal blood circuit. The control system 720 can be communicably coupled to one or more local server systems 722, which can be configured for data storage locally and/or communicably coupled to one or more remote server systems 724 via a network such as the internet. The control system 720 can also include user interface components such as a display, keyboard, or mouse. These components can be used to adjust various parameters and view various reports that may be generated and/or displayed based on the processes executed by the control system. The report content and/or format may be customized by a user. For example, a display can show data logs created that maintain a record of what supplemental fluids were infused, the quantity of those fluids infused, the time of the infusion, the reason for infusion, and the results (e.g. sensed parameters of the blood fluid, post infusion) of those infusions. The storage system of the control system 720 can retain this information in a database that can be cataloged based on the patient treated. The storage system of the control system 720 can receive information about the patient being treated in the form of a patient profile containing information specific to the patient or information regarding acceptable or normal values for blood parameters for patients having biometrics within certain ranges, e.g., age, height, weight, and/or sex, that can be relevant to the infusion protocol initiated by the control system 720 over a treatment cycle. In certain implementations, the control system 720 is configured to operate in a feedback control loop to continue infusing the supplemental fluid source into the blood until a target value is reached. In such implementations, after an initial infusion is applied, a new sensor reading, for example via arterial sensor 729 positioned on arterial line 728 is taken of the infused fluid to determine whether or not any further infusions are required. The pump 704 controls pumping of the infused blood from conduit 726, through the venous line and to the arterial line 728 for circulating back to the patient. In some implementations, a sensor 730 may be positioned upstream of the pump 704 and downstream of the venous line to determine if the infused blood flowing through conduit 726 is infused prior to pumping it back to the patient. The system 700 includes an oxygenator 731 fluidly coupled to the blood circuit and configured to provide oxygen to the blood from the patient. The system may include an arterial filter and one or more sensors sensing parameters of the blood post oxygenation. The system may also include a recirculation line 734 downstream of the pump that is selectively communicatively coupled (i.e., via recirculation valve 732) with arterial line 728 to recirculate the blood (e.g. for further infusion) prior to returning it to the patient. The system may include a fluid flow regulator, e.g., a needle valve 732, which controls the flow of oxygen gas into the blood circuit, to adjust the flow rate of oxygen gas delivered to or infused into the blood circuit (via the oxygenator). The system may include a fluid flow regulator, e.g., an electronic gas blender 733 (which is in fluid communication with the blood carrying conduit and/or an oxygenator of the extracorporeal circulatory support system) to adjust the percentage of oxygen gas delivered to or infused into the blood circuit (via an oxygenator).

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device.

A computer program is a set of instructions that can be used, directly or indirectly, in a computer to perform some activity or bring about some result. A computer program can be written in any form of programming language, including compiled or interpreted languages, and it can be deployed in any form, including as a stand-alone program or as a module, component, subroutine, or other unit suitable for use in a computing environment. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks.

The computing device described herein may include, or be operatively coupled to communicate with, one or more mass storage devices for storing data files; such devices include magnetic disks, such as internal hard disks and removable disks; magneto-optical disks; and optical disks.

The terms "machine-readable medium," "computer-readable medium," and "processor-readable medium" as used herein, refer to any medium that participates in providing data that causes a machine to operate in a specific fashion. Using a computer system, various processor-readable media (e.g., a computer program product) might be involved in providing instructions/code to processor(s) for execution and/or might be used to store and/or carry such instructions/code (e.g., as signals).

In many implementations, a processor-readable medium is a physical and/or tangible storage medium. Such a medium may take many forms, including but not limited to, non-volatile media and volatile media. Non-volatile media include, for example, optical and/or magnetic disks. Volatile media include, without limitation, dynamic memory.

Common forms of physical and/or tangible processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of processor-readable media may be involved in carrying one or more sequences of one or more instructions to one or more processors for execution. Merely by way of example, the instructions may initially be carried on a flash device, a device including persistent memory, and/or a magnetic disk and/or optical disc of a remote computer. A remote computer might load the instructions into its dynamic memory and send the instructions as signals over a transmission medium to be received and/or executed by a computer system.

The computing device may be part of a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet. The computer system can include clients and servers. A client and server are generally remote from each other and typically interact through a network, such as the described one. The relationship of client and server arises by virtue of computer programs running on the respective computers and having a client-server relationship to each other.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

Information and signals may be represented using any of a variety of different technologies and techniques. For example, data, instructions, commands, information, signals, and symbols that may be referenced throughout the above description may be represented by voltages, currents, electromagnetic waves, magnetic fields or particles, optical fields or particles, or any combination thereof.

The methods, systems, and devices discussed above are examples. Various alternative configurations may omit, substitute, or add various procedures or components as appropriate. Configurations may be described as a process which is depicted as a flow diagram or block diagram. Although each may describe the operations as a sequential process, many of the operations can be performed in parallel or concurrently. In addition, the order of the operations may be rearranged. A process may have additional stages not included in the figure. Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional stages or functions not included in the figure. Furthermore, examples of the methods may be implemented by hardware, software, firmware, middleware, microcode, hardware description languages, or any combination thereof. When implemented in software, firmware, middleware, or microcode, the program code or code segments to perform the tasks may be stored in a non-transitory processor-readable medium such as a storage medium. Processors may perform the described tasks.

Components, functional or otherwise, shown in the figures and/or discussed herein as being connected or communicating with each other are communicatively coupled. That is, they may be directly or indirectly connected to enable communication between them.

As used herein, including in the claims, "and" as used in a list of items prefaced by "at least one of" indicates a disjunctive list such that, for example, a list of "at least one of A, B, and C" means A or B or C or AB or AC or BC or ABC (i.e., A and B and C), or combinations with more than one feature (e.g., AA, AAB, ABBC, etc.). As used herein, including in the claims, unless otherwise stated, a statement that a function or operation is "based on" an item or condition means that the function or operation is based on the stated item or condition and may be based on one or more items and/or conditions in addition to the stated item or condition.

Having described several example configurations, various modifications, alternative constructions, and equivalents may be used without departing from the disclosure. For example, the above elements may be components of a larger system, wherein other rules may take precedence over or otherwise modify the application of the invention. Also, a number of operations may be undertaken before, during, or after the above elements are considered. Also, technology evolves and, thus, many of the elements are examples and do not bound the scope of the disclosure or claims. Accordingly, the above description does not bound the scope of the claims. Further, more than one invention may be disclosed.

Other embodiments are within the scope of the invention. For example, due to the nature of software, functions described above can be implemented using software, hardware, firmware, hardwiring, or combinations of any of these. Features implementing functions may also be physically located at various locations, including being distributed such that portions of functions are implemented at different physical locations.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

What is claimed is:

1. A system for controlling infusion of one or more supplements into blood received from a patient, the system comprising:
    at least one extracorporeal circulatory support system comprising:
        a pump,
        a plurality of fluid conduits fluidly coupled to the pump through which the blood flows, and
        at least one sensor configured to measure one or more parameters representing an oxygen content of the blood;
    at least one fluid flow regulator coupled to the at least one extracorporeal circulatory support system; and
    a processor, a memory, and associated circuitry communicatively coupled to the at least one sensor and the at least one fluid flow regulator, wherein the processor is configured to:
        receive one or more signals corresponding to a measured value of each of the one or more parameters of the blood from the at least one sensor,
        determine one or more target values for the one or more parameters representing the oxygen content of the blood received from the patient, the one or more target values being based on a patient profile and the measured value of each of the one or more parameters,
        control the at least one fluid flow regulator to infuse at least one supplemental fluid from a supplemental fluid source into the blood, the at least one supplemental fluid comprising an oxygen-infused fluid, the at least one supplemental fluid configured to modify the oxygen content of the blood, wherein the infusion is based on the target value for the oxygen content of the blood, and
        receive one or more additional signals from at least one additional sensor configured to measure the oxygen content of the blood when the at least one supplemental fluid is infused into the blood, and wherein the processor is configured to cause additional infusion of the at least one supplemental fluid when the measured oxygen content is outside of a target range to modify the oxygen content of the blood.

2. The system according to claim 1, wherein the processor is configured to receive data corresponding to a parameter of the at least one supplemental fluid infused into the blood.

3. The system according to claim 2, wherein the processor is configured to cause the at least one sensor to measure the one or more parameters of the blood after the infusion of the at least one supplemental fluid, and to continue infusion if a value, that is measured post-infusion, of the one or more parameters of the blood does not correspond to the one or more target values or reduce infusion if the value of the one or more parameters of the blood corresponds to the target value.

4. The system according to claim 3, wherein the processor is configured to cause the patient profile to be updated during a treatment cycle based on one or more of the measured one or more parameters of the blood after the infusion of the at least one supplemental fluid.

5. The system according to claim 1, wherein the patient profile comprises a log comprising patient data from the patient being treated or acceptable or normal values for blood parameters for patients having biometrics within predefined ranges.

6. The system according to claim 5, wherein the processor is configured to access the patient profile via the memory to determine the one or more target values for the one or more parameters of the blood received from the patient.

7. The system according to claim 5, wherein the processor is configured to access the patient profile via a remote server to determine the one or more target values for the one or more parameters of the blood received from the patient.

8. The system according to claim 1, wherein the at least one extracorporeal circulatory support system comprises an extracorporeal membrane oxygenation machine.

9. The system according to claim 8, wherein the at least one extracorporeal circulatory support system comprises an automated clamp or valve and wherein the processor is configured to cause one or more supplemental fluids from the supplemental fluid source to be infused during an unclamped phase or open valve phase.

10. The system according to claim 8, wherein the at least one extracorporeal circulatory support system comprises an automated clamp or valve and wherein the processor is configured to cause one or more supplemental fluids from the supplemental fluid source to be infused during a partially open valve phase permitting regulated flow of the supplemental fluid, and wherein the fluid flow regulator comprises an infusion pump and wherein the processor is configured to cause regulated infusion of one or more supplemental fluids from the supplemental fluid source.

11. The system according to claim 8, wherein the extracorporeal membrane oxygenation machine comprises an oxygenator.

12. The system according to claim 11, wherein the extracorporeal membrane oxygenation machine comprises an arterial filter positioned downstream of the oxygenator.

13. The system according to claim 11, wherein the extracorporeal membrane oxygenation machine comprises a bubble sensor.

14. The system according to claim 13, wherein the extracorporeal membrane oxygenation machine comprises a pressure sensor.

15. The system according to claim 1, wherein the supplemental fluid source comprises a plurality of supplemental fluid sources and wherein the processor is configured to select a supplemental fluid source from the plurality of supplemental fluid sources based on the one or more target values of the one or more parameters for the blood.

16. The system according to claim 15, wherein the plurality of supplemental fluid sources comprises blood, saline, and medication.

17. The system according to claim 1, wherein the at least one sensor comprises an infusion sensor configured to measure one or more of a duration, a flow rate, and a pressure of the supplemental fluid infused into the blood.

18. The system according to claim 17, comprising an alarm system communicably coupled to the processor and configured to provide a notification when the supplemental fluid source is infused into the blood.

19. The system according to claim 1, further comprising one or more other sensors configured to measure one or more additional parameters of the blood, the one or more additional parameters representing a hemoglobin content in the blood, a hematocrit content in the blood, a blood pH, a $CO_2$ level in the blood, an $SO_2$ level in the blood, a $pCO_2$ level in the blood, or a $pO_2$ level in the blood.

20. The system according to claim 1, further comprising:
    a recirculation line downstream of the pump configured to recirculate the supplemental fluid, wherein the processor is configured to further modify the oxygen content of the blood by recirculation of the supplemental fluid.

* * * * *